(12) United States Patent
Chen et al.

(10) Patent No.: US 11,364,299 B2
(45) Date of Patent: Jun. 21, 2022

(54) NON-ADDICTIVE ANALGESIC SUSTAINED-RELEASE DRUG DELIVERY SYSTEM AND PREPARATION METHOD THEREOF

(71) Applicant: LIPONT PHARMACEUTICALS INC., Richmond (CA)

(72) Inventors: Tao Chen, Shaanxi (CN); Wudang Lu, Shaanxi (CN); Weiping Yu, Shaanxi (CN); Jianli Gao, Shaanxi (CN); Danfeng Kong, Shaanxi (CN); Qingchuan Zhao, Shaanxi (CN); Weijiao Wang, Shaanxi (CN); Qinyuan Wu, Shaanxi (CN)

(73) Assignee: LIPONT PHARMACEUTICALS INC., Richmond (CA)

( * ) Notice: Subject to any disclaimer, the term of this patent is extended or adjusted under 35 U.S.C. 154(b) by 194 days.

(21) Appl. No.: 14/762,573

(22) PCT Filed: Apr. 10, 2013

(86) PCT No.: PCT/CN2013/074010
§ 371 (c)(1),
(2) Date: Jul. 22, 2015

(87) PCT Pub. No.: WO2014/114032
PCT Pub. Date: Jul. 31, 2014

(65) Prior Publication Data
US 2015/0359891 A1    Dec. 17, 2015

(30) Foreign Application Priority Data

Jan. 22, 2013 (CN) .......................... 201310022657.3

(51) Int. Cl.
| | | |
|---|---|---|
| *A61K 47/10* | (2017.01) | |
| *A61K 47/14* | (2017.01) | |
| *A61K 47/44* | (2017.01) | |
| *A61K 31/445* | (2006.01) | |
| *A61K 9/00* | (2006.01) | |
| *A61K 9/08* | (2006.01) | |
| *A61K 31/135* | (2006.01) | |
| *A61K 31/245* | (2006.01) | |
| *A61K 31/381* | (2006.01) | |
| *A61K 31/42* | (2006.01) | |
| *A61K 31/47* | (2006.01) | |
| *B65B 3/00* | (2006.01) | |
| *B65B 7/16* | (2006.01) | |
| *B65B 31/00* | (2006.01) | |

(52) U.S. Cl.
CPC ............ *A61K 47/10* (2013.01); *A61K 9/0019* (2013.01); *A61K 9/08* (2013.01); *A61K 31/135* (2013.01); *A61K 31/245* (2013.01); *A61K 31/381* (2013.01); *A61K 31/42* (2013.01); *A61K 31/445* (2013.01); *A61K 31/47* (2013.01); *A61K 47/14* (2013.01); *A61K 47/44* (2013.01); *B65B 3/003* (2013.01); *B65B 7/161* (2013.01); *B65B 31/003* (2013.01)

(58) Field of Classification Search
CPC ........ A61K 47/10; A61K 9/0019; A61K 9/08; A61K 31/135; A61K 31/245; A61K 31/381; A61K 31/42; A61K 31/445; A61K 31/47; A61K 47/14; A61K 47/44; B65B 3/003; B65B 7/161; B65B 31/003
See application file for complete search history.

(56) References Cited

U.S. PATENT DOCUMENTS

| | | | |
|---|---|---|---|
| 7,648,711 B2 | 1/2010 | Wang et al. | |
| 2010/0041704 A1* | 2/2010 | Aberg ..................... | A61P 23/00 514/330 |
| 2013/0156853 A1 | 6/2013 | Zhang et al. | |

FOREIGN PATENT DOCUMENTS

| | | |
|---|---|---|
| CN | 1533764 A | 10/2004 |
| CN | 101926757 A | 12/2010 |
| WO | WO 2003/077885 A2 | 9/2003 |
| WO | WO 2007/070679 A2 | 6/2007 |
| WO | WO 2011/121034 A2 | 10/2011 |

OTHER PUBLICATIONS

International Searching Authority, International Search Report for International Application No. PCT/CN2013/074010, dated Oct. 31, 2013, 12 pages, State Intellectual Property Office of the P.R.C., China.
European Patent Office, Extended European Search Report for application No. 13872302.8, dated Mar. 21, 2016, 14 pages, Germany.
Kaufman, Eliezer, et al., "Preemptive Analgesia and Local Anesthesia as a Supplement to General Anesthesia: A Review", *Anesthesia Progress*, Mar. 2005, pp. 29-38, vol. 52, No. 1, American Dental Society of Anesthesiology, U.S.

(Continued)

*Primary Examiner* — James D. Anderson
*Assistant Examiner* — William Y Lee
(74) *Attorney, Agent, or Firm* — Alston & Bird LLP

(57) ABSTRACT

A non-addictive analgesic sustained-release drug delivery system, comprising: (1) a narcotic analgesic drug having a concentration of 1 mg/ml-160 mg/ml, the drug being selected from a group consisting of: a local analgesic drug, and the combination of the local analgesic drug and a nonsteroidal analgesic drug and/or an opioid analgesic drug; (2) a drug menstruum in a proportion of 1%-75% (v/v), the menstruum being selected from a group consisting of benzyl alcohol, ethanol, benzyl benzoate, ethyl lactate, and tetrahydrofurfuryl polyethylene glycol ether; and (3) a drug sustained-release formulation having a proportion of 25%-99% (v/v), the sustained-release formulation being selected from a group consisting of natural vegetable oil, synthetic lipid, artificially improved half-natural lipid and derivative thereof. Also disclosed are a preparation process and use of the sustained-release drug delivery system.

2 Claims, 5 Drawing Sheets

(56) References Cited

OTHER PUBLICATIONS

Lich, Robert, et al., "The Symptomatic Treatment of Acute Epididymitis", *American Journal of Surgery*, Dec. 1940, pp. 633-634, vol. 50, No. 3, Paul Hoeber, U.S.
Moran, Timothy F., "Evaluation of the Various Methods to Manage Postoperative Pain and Morbidity Following Anorectal Surgery", *American Journal of Surgery*, Jan. 1957, pp. 102-107, vol. 93, No. 1, Paul Hoeber, U.S.
Perlow, Samuel, et al., "Surgical Relief Of Pain Due to Circulatory Disturbances of the Feet, Report of a New Method", *American Journal of Surgery*, Jul. 1939, pp. 104-109, vol. 45, No. 1, Paul Hoeber, U.S.
Pupka, Artur, et al., "[The usage of Synthol in the body building]", *Polimery W Medycynie-Polymers In Medicine—Polymers In Dermedizin*, Jan. 2009, pp. 63-65, vol. 39, No. 1, Panstwowe Wydawnictwo Naukowe, Poland.
Office Action for Japanese Application No. 2015-554013 dated Sep. 9, 2016.
Office Action for Korean Application No. 10-2015-7022974 dated Sep. 1, 2016.
Office Action for European Application No. 13872302.8 dated May 22, 2018.
Written Opinion for International Application No. PCT/CN2013/074010 dated Oct. 21, 2013.
"Local Anesthetics" Ch. 6, Local anestetics and derivatives, Section 4 Ropivacaine, dated 2009.
Xiong, B. et al., "Efficacy of Wound Infiltration with Ropivacaine on Postoperative Pain relief after Acute Appendectomy in Children", Department of Anesthesia, Children's Hospital of Fudan University, dated May 2008, pp. 573-577.
Xiao, J. "Clinical observation of different concentrations of ropivacaine in labor analgesia", Department of Anesthesia, dated 2007.
Tang, J. et al., "Progress on Postoperative Pain and Acesodyne", Journal of Dali Medical College, China Academic Journal Electronic Publishing House, dated 2000.
Miller, R. "Miller's Anesthesia" Ropivacaine, dated 2004.
Rowe, R. et al., "Handbook of Pharmaceutical Excipients" Sixth Edition, dated 2009, pp. 1-34.
Sakellaris, G. et al., "Effects of Ropivacaine Infiltration on Cortisol and Prolactin Responses to Postoperative Pain after Inguinal Hernioraphy in Children", University of Crete, Greece Journal of Pediatric Surgery, dated Oct. 2004.
Wu, S. et al., "Clinical observation of low concentration ropivacaine hydrochloride combined with Fentanyl for patient controlled epidural labor Anaigesia", dated 2008.
Chen, S. "A Comparison of Ripovacaine and Bupivacaine on Gynecologic Postoperative Pain", Juijiang Medical Journals, dated Mar. 17, 2002, pp. 133-134.
Yang, Z. et al., "The value of continuous epidural Infusion of 0.1% 0.1% Ropivacaine and 0.1% bupivacaine for Post-operative Analgesia in Elderly patients" Department of Anesthesiology, dated 2008.
Niiyama, Y. et al., "The Addition of Epidural Morphine to Ropivacaine Improves Epidural Analgesia After Lower Abdominal Surgery", Regional Anesthesia and Pain, Canadian Journal of Anesthesia, 52:2, dated 2005, pp. 181-185.
Chen, S. "A Comparison of Ripovacaine and Bupivacaine on Gynecologic Postoperative Pain", Jiujiang Medical Journals, dated Mar. 17, 2002, pp. 133-134.
Corresponding Indonesian Application No. P00201505151 Office action dated Oct. 31, 2019 (3 pages).

* cited by examiner

NON-ADDICTIVE ANALGESIC SUSTAINED-RELEASE DRUG DELIVERY SYSTEM AND PREPARATION METHOD THEREOF

CROSS REFERENCE TO RELATED APPLICATIONS

This application is a national stage application, filed under 35 U.S.C. § 371, of International Application No. PCT/CN2013/074010, filed Apr. 10, 2013, which claims priority to Chinese Patent Application No. 201310022657.3, filed Jan. 22, 2013, the contents of both of which as are hereby incorporated by reference in their entirety.

BACKGROUND

Technical Field

The present invention relates to the field of pharmacology, particularly to a non-addictive local anesthetic analgesic sustained-release drug delivery system.

Currently, pain is regarded as the fifth vital sign of human body in addition to breathing, pulse, body temperature and blood pressure, and is classified into acute and chronic pains. Post-operative pain, as acute pain, is a complex physical and psychological reaction in the tissue injury and repairmen process in the body, inevitably encountered by all post-operative patients, and is one of the most urgent problems that need to be dealt with in current clinical post-operative practice.

In recent years, with continuing progression in researches on neuroscience and fundamental pain theory, more in-depth understanding of the mechanism (at molecular level) of the occurrence of post-operative pain has been acquired, and it is commonly recognized by researchers over the world that post-operative pain is different from normal physical pain while, besides injured feelings induced by mechanical injury to neural endings brought by surgical wounds, change in peripheral system sensitivity resulted from the release of inflammatory mediators followed by tissue lesion is also one of the reasons causing post-operative pain. The principle mechanism is regarded as follows: stimulation from a post-operative lesion leads to a reverse cytoplasmic flow in peripheral neuronal axons and consequently the release of substance P by neural endings, resulting in local increase in vascular permeability and occurrence of tissue edema; meanwhile, inflammatory algogenic substances such as bradykinin, histamine, leukotriene, PG and other arachidonic acid metabolites released by injured tissues may both directly stimulate nociceptors and lead to peripheral neural activation and sensitization, resulting in pain caused by even normal subthreshold stimulus (such mechanism is very similar to that of acute inflammatory pain). It was discovered from recent research results that nociceptive stimulus induced by operative lesion might also promote central sensitization so that central nerves respond to peripheral pain stimuli with a lowered threshold and extended time.[1]

Furthermore, post-operative pain has great impacts on function of various organs in patients, and may cause changes in a series of pathological and physiological parameters, for example, abnormality in autonomic nervous activities resulted from pain, elevating of blood catecholamine, increase in glucagon secretion, insulin secretion reducing hyperglycemia, increase in adrenocorticotropin secretion, increase in secretion of cortisol, aldosterone, and antidiuretic hormone, and the like. The impacts with respect to physiological function are primarily demonstrated in the following aspects: 1) mental and psychological influence: pain may lead to agitation, dejection, fear, anxiety, depression or character changes in patients; 2) changes in cardiovascular system: elevation of blood catecholamine quickens heart rate, myocardial contractility is enhanced, cardiac output increases, peripheral blood vessels contract, systemic vascular resistance increases, blood pressure elevates, and severe pain may even lead to painful shock; 3) changes in autonomic nervous system: autonomic nervous function disorders such as sleep disorder, lack of appetite, nausea and vomiting, constipation, sweating, and blood pressure fluctuation may occur; 4) changes in immune system: pain mainly causes decrease in immunoglobulin, delaying of body recovery, lowering of phagocyte function at various degrees, inhibition to humoral and cellular immune functions to a certain extent, slowing of protein synthesis and acceleration of protein degradation in vivo, and affects wound healing; 5) social damage: with a high incidence, pain is hard to diagnose, has an extended course, tremendous medical resource costs and treatment expenses, and individual pain may have impacts on the whole family and neighbors, whereby the quality of civil lives is greatly deteriorated.[2]

Post-operative analgesia can not only reduce post-operative pain, but also stable patient's physiological indexes, that can cut down complication probability in perioperative period, and has remarkable effect on improving prognosis and shortening hospitalization. Currently, the clinical post-operative analgesia and the route of administration are mainly shown below:

With regard to clinical drugs:

1. Opioid analgesics: morphine, fentanyl, sufentanil, buprenorphine, tramadol, alfentanil, remifentanil and the like;

2. Anesthetic infiltration drugs (non-addictive): lidocaine, procaine, ropivacaine, bupivacaine, levobupivacaine, tetracaine, benzocaine, dyclonine and the like;

3. Nonsteroidal anti-inflammatory analgesics: aspirin, indomethacin, aminopyrine, phenylbutazone and the like.

Drug delivery method:

1. Traditional administration methods: oral administration or intramuscular injection (systemic administration, central administration) of opioid analgesics, for example, has strong analgesic effects together with prominent adverse effects, and repeated use thereof tends to results in drug-dependency, dizziness, nausea, vomiting, constipation, urine retention, drowsiness, respiratory depression, mental disorder, nervous system toxicity and the like;

2. Novel administration methods: patient-controlled analgesia (intravenous infusion, epidural infusion, ventricular), percutaneous administration (such as fentanyl patches), administration into body cavities, infusion with intravenous infusion pump at a constant speed, balanced analgesia, preemptive analgesia, administration to epidural space, oral mucosal administration, nasal mucosal administration and the like (target site administration).

In future researches on post-operative analgesia, anesthetics, novel opioid drugs, sustained-release formulations of nonsteroidal analgesics, multi-mode analgesia, and surgical site proximity nerve block will be the focus in the related field for the primary purpose of improving analgesic intensity and reducing adverse reactions, for example, continuous peripheral nerve block, patient-controlled regional analgesia techniques, and local nerve block techniques, as well as mid-humerus brachial plexus block, lumber plexus block, femoral nerve-sciatic nerve block and the like.

The history of local anesthetics has been more than 150 years since the discovery and use thereof. As early as in 1860, Albert Niemann, student of German chemist Friedrich Wohler, extracted an alkaloid from coca leaves in a laboratory of the University of Gottingen and named it cocaine. In 1884, under Freund's advice, Koller used cocaine in eye surgeries and achieved excellent effects; in the next year, Halstead and Corning used cocaine in mandibular nerve block and dog spinal anesthesia experiments respectively, which was regarded as the beginning of use of this drug in local nerve block and epidural nerve block. Procaine was discovered by Einhron in 1904 and applied clinically by Braum in the next year. Tetracaine was synthesized by Firsleb in 1928, lidocaine by Lofgren and Lundguist in 1943, and a series of local anesthetics, such as benzocaine, dibucaine, bupivacaine, prilocaine, and mepivacaine, appeared thereafter. Up till now, two classes of local anesthetics, including the ester-type and the amide-type, have been established.

Ropivacaine is a long-acting amide-type local anesthetic synthesized in recent years, and, as a result of further optimization of bupivacaine, has a fundamental structure of 1-propy 1-2,6-pipeco loxylidide laevo isomer, pH 7.4, pKa 8.1, low liposolubility and a high dissociation constant. Therefore, the sensitivity thereof to C fibers is substantially higher than to A fibers, and a clear phenomenon of discrimination of motor nerve block from sensory nerve block is demonstrated. Epidural absorption of ropivacaine molecules shows a dimorphic profile, with a half-time of fast phase of 14 min and a half-time of slow phase of 4 h. Ropivacaine predominantly associates with plasma proteins (94%) in a concentration-dependent manner with a steady distribution volume of 47 L. Ropivacaine acts in the same mechanism as that of local anesthetics such as procaine, lidocaine, and bupivacaine, by inhibiting neural cell sodium channels and blocking nerve excitation and conduction.[3,4]

With constant progression in researches on ropivacaine action mechanism and continuing exploration in clinical applications, the analgesic efficacy of ropivacaine used alone or in combination with opioid drugs has been established clinically in a wide range. Such efficacy may be generalized in the following aspects: 1) local infiltration anesthetic analgesia (ropivacaine was used both pre- and post-operatively by Sakellaris et al.[5] in performing descending inguinal herniorrhaphy under general anesthesia, showing a substantial and lasting analgesic effect with few adverse reactions, which was superior than a fentanyl controlled-release percutaneous patch group); 2) nerve block (Qihong ZHAO et al.[6] conducted comparative researches on transaxillary brachial plexus block using ropivacaine at different concentrations, and recognized that 0.375% ropivacaine had faster onset, better efficacy, and fewer adverse effects as compared to 0.25% bupivacaine); 3) post-operative analgesia (Niiyama et al[7] conducted clinical trials in 60 lower abdominal surgical patients by randomly dividing the patients into a ropivacaine group, a morphine group, and a combined ropivacaine-morphine group and epidurally administrating the analgesics, with the results showing a better effect in the combined administration group; the results of clinical researches conducted by Zhanmin YANG et al. further demonstrated that the combined application of ropivacaine with opioid analgesics was able to remarkably reduce the usage of the opioid analgesics, with a longer-lasting efficacy and fewer adverse reactions); 4) gynecologic labor analgesia (clinical researches conducted by Shengjiao WU and Jinhui XIAO et al.[8,9] clearly demonstrated that ropivacaine in combination with opioid drugs applied in epidural anesthesia or combined spinal and epidural anesthesia for labor analgesia was clearly effective, with little block to motor nerves and no impact on stages of labor and newborns, and was an ideal drug for labor analgesia at present); 5) gynecologic post-operative analgesia (the clinical research results of Shunfu CHEN and fellow researchers[10] showed that ropivacaine was more suitable for patient-controlled analgesic local anesthesia in gynecologic post-operative patients than bupivacaine); 6) pediatric analgesia (Bo XIONG et al.[11] believed that the post-operative local infiltration analgesic effect with 0.175% ropivacaine was similar to that with morphine, with lower incidence of nausea and vomiting); 7) analgesia in senile patients (researches conducted by Zonglin YANG et al.[12] demonstrated that the analgesic effect of continuous epidural infusion with 0.1% ropivacaine in elderly patients having received lower limb surgeries was comparable to that with 0.1% bupivacaine and ropivacaine exhibited a relatively lower cardiac toxicity and higher safety in use).

Numerous clinical research results indicate that ropivacaine has clear effects in anesthesia and pain treatment, low cardiac toxicity, long action duration (analgesia may last for about 8 hours with one clinical injection) and so on due to its unique physical and chemical characteristics, i.e., distinct discrimination of sensory-motor nerve block at low concentrations, suggesting it may have more broad range of clinical application in the future.

However, current clinical investigation results show that such local anesthetics have only a few clinical formulations, i.e., common hydrochloride salt or methansulfonate salt solution. Thus, preparation of non-addictive sustained-release formulations by using the local anesthetics as principle agents may not only increase clinical application varieties of such anesthetics but also extend the range of the clinical application thereof, decrease the number of doses given clinically, and reduce clinical adverse reactions thereof, showing great promise in clinical development. Results from patent searches indicate that there is currently now patent application related to sustained-release formulations of such drugs. On the basis of this fact, the applicant, Lipont Pharmaceuticals Inc, develops formulation and preparation methods of non-addictive analgesic sustained-release formulations useful for clinical post-operative analgesia.

REFERENCES

1. Wangjun TANG, Guangfen YIN et al, Progress in post-operative pain and analgesia [J] Journal of Dali Medical University 2000, 2 (9): 68-70.
2. Shanglong YAO, Huaqing SHU, Develeopment in pain therapeutics [J] Journal of Clinical Internal Medicine, 2005, 22 (12): 793-796.
3. Shitong L I, Xinliang ZHUANG, Local Anesthetics 1th 2009 76-83.
4. Strichartz G R, Berde C B. Local Anesthetics. In: Ronald D. Miller: Miller's Anesthesia. 6th edition.
5. Sakellaris G, Petrakis I, Makatounaki K, et al. Effects of ropivacaine infiltration on cortisol and prolactin responses to post operative pain after inguinal hernioraphy in children. Pediatr Surg, 2004, 39(9):1400
6. Qihong ZHAO, Peng WEI, Wentao DAI, Comparative researches on transaxillary brachial plexus block using ropivacaine at different concentrations [J] Applied Journal of General Practice, 2007, 5(4):2931

7. Niiyama Y, Kawamata T, Shimizu H, et al. The addition of epidural morphine to ropivacaine improves epidural analgesia after lower abdominal surgery. Can J Anaesth, 2005, 52(2): 181
8. Jinhui XIAO, Clinical observation on application of ropivacaine at different concentrations in labor analgesia, [J] Modern Chinese Doctor, 2007, 45(6):111
9. Shengjiao W U, Wenli CHENG, Feng GUO et al., Clinical observation of low concentration of ropivacaine hydrochloride in combination with fentanyl in epidural self-controlled labor analgesia [J] Jiangxi Medical Journal, 2008, 43(1):361.
10. Shunfu CHEN, Comparison of gynecologic post-operative analgesic effect of ropivacaine and bupivacaine [J] Jiujiang Medicine, 2002, 17(3):1331.
11. Bo XIONG, Qiqing SHI, Xuan WANG, Effect of local ropivacaine infiltration on post-op pain in pediatric appendectomy [J] Chinese Journal of Clinical Pharmacology and Therapeutics, 2008, 13(5):5731.
12. Zonglin YANG, Rongzhi ZHENG, Yuqin ZHANG, Merits of continuous epidural infusion with 0.1% ropivacaine and 0.1% bupivacaine in post-op analgesia in elderly patients having received lower limb surgeries [J] Shaanxi Medical Journal, 2008, 37(2):2461.

BRIEF SUMMARY

An objective of the present invention is to provide a novel non-addictive local anesthetic analgesic sustained-release drug delivery system having anesthetic analgesics as the principle agent, which system includes local anesthetics used alone and also includes one or a mixture of two or more of local anesthetics, opioid analgesics (at non-addictive low or medium dose), and nonsteroidal anti-inflammatory analgesics as well as menstruum and corresponding sustained-release agents.

The drug delivery system according to the present invention may be recognized as a pharmaceutical composition, a pharmaceutical prescribed composition, a formula or a pharmaceutical formulation.

Such drug delivery system is characterized in that it is an oily or oily solution-type drug delivery system and has good formulation stability and homogeneity.

The analgesics in the drug delivery system have a fundamental feature of being non-addictive, and include anesthetic and non-anesthetic analgesics.

Anesthetic analgesics refers to local anesthetics, mainly including a free base of procaine, lidocaine, bupivacaine, levobupivacaine, ropivacaine, tetracaine, dibucaine, and etidocaine (the free base being preferred), as well as salts thereof including methanesulfonate, hydrochloride, citrate, sulfate, lactate, succinate, fumarate, glutamate, ethylsulfonate, benzenesulfonate, citrate, salicylate, and maleate thereof, and the anesthetic analgesics may be one or a composition of two or more of the above. Among the above, the ropivacaine free base and salts thereof are preferred, and the anesthetic analgesics may be one or a composition of two or more of these. Among others, the ropivacaine free base is the most effective.

Non-anesthetic analgesics mainly include nonsteriodal anti-inflammatory drugs and opioid drugs (at non-addictive low or medium dose).

Nonsteriodal anti-inflammatory drugs include, among others, aspirin, diclofenac sodium, ibuprofen, naproxen, nabumetone, sulindac, mefenamic acid, clofenamic acid, diclofenac acid, flufenamic acid, piroxicam, meloxicam, aminopyrine, analgin, phenacetin, paracetamol, parecoxib, rofecoxib, valdecoxib, and nimesulide.

Opioid drugs include, among others, dihydromorphinone, dezocine, naloxone, naltrexone, morphine, fentanyl, sufentanil, codeine, pethidine, pentazocine, methadone, etorphine, bucinnazine, buprenorphine, tramadol, alfentanil, and remifentanil.

Further, in addition to local anesthetics alone, the analgesics may also be one or a mixture formed from two or more of local anesthetic analgesics, nonsteroidal anti-inflammatory analgesics and opioids (at non-addictive low or medium dose); or one or a mixture formed from two or more of local anesthetic analgesics and nonsteroidal anti-inflammatory analgesics; and may also be one or a mixture formed from two or more of local anesthetic analgesics and opioid analgesics (at non-addictive low or medium dose).

It is emphasized that the administrated dose of the opioid analgesics used in the formulations is a non-addictive medium, low or micro dose.

The nonsteroidal anti-inflammatory drugs and opioid analgesics used in the formulations may be present in a form of free state, or corresponding salts when combined with acids or bases, and the analgesics is optionally one or a mixture of two or more of those.

The analgesic sustained-release drug delivery system according to the present invention comprises anesthetic analgesics as pharmaceutically active component and liquid adjuvants, wherein the anesthetic analgesics are at a concentration of 1-160 mg/ml (w/v). The liquid adjuvants consist of drug menstruum in a proportion of 1%-75% (v/v) and drug sustained-release agents in a proportion of 25%-99% (v/v).

On the basis of the above proportions of the principle agent and adjuvants in the composition, the drug delivery system preferably consists of analgesics at a concentration of 1-90 mg/ml (w/v) and adjuvants preferably consisting of drug menstruum in a proportion of 1%-50% (v/v) and drug sustained-release agents in a proportion of 50%-99% (v/v).

Most preferably, the drug delivery system consists of analgesics at a concentration of 12-50 mg/ml (w/v) and adjuvants consisting of drug menstruum in a proportion of 10%-40% (v/v) and drug sustained-release agents in a proportion of 60%-90% (v/v).

The drug menstruum and sustained-release agent are selected with reference to current products available on the market, and the examples selected are mostly oily long-acting intramuscular injection agents, as generally shown in the table below:

TABLE I

Summary of a part of common oily long-acting intramuscular injection agents available on the market

| Product name | Principle agent | Manufacturer | Oil phase | Non-aqueous solvent | Note |
|---|---|---|---|---|---|
| PROLUTON DEPOT | Hydroxyprogesterone caproate | Schering HC | castor oil | benzyl benzoate (46%) | |

TABLE I-continued

Summary of a part of common oily long-acting intramuscular injection agents available on the market

| Product name | Principle agent | Manufacturer | Oil phase | Non-aqueous solvent | Note |
|---|---|---|---|---|---|
| TOCOGESTAN | Progesterone | Theramax | ethyl oleate | benzyl benzoate (40%) | |
| DELESTROGEN | Estradiol valerate | BMS | castor oil | benzyl alcohol (20%), ethanol, benzyl benzoate | |
| DELALUTIN | Progestogen | BMS | castor oil | benzyl alcohol, ethanol, benzyl benzoate | |
| NORISTERAR | Norethisterone enanthate | — | castor oil | — | contraceptive |

Drug menstruum refers to natural or artificially synthesized organic solvents or mixture of solvents that dissolves local anesthetic analgesics (including one or a mixture of two or more of local anesthetic analgesics) or dissolves local anesthetic analgesics, opioid analgesics (at non-addictive low or medium dose) and nonsteroidal anti-inflammatory analgesics.

The drug menstruum advantageously includes one or a mixture of two or more of benzyl alcohol, ethanol, glyceryl monoacetate, ethyl lactate (a green solvent, pharmaceutical adjuvant, with low toxicity), tetrahydrofurfuryl polyethylene glycol ether (Handbook of Pharmaceutical Adjuvants, $4^{th}$ edition, RC LUO ed., UK, translated by Junmin ZHENG, page 313-314), and benzyl benzoate, among which one or a mixture of two or more of ethanol, benzyl alcohol, benzyl benzoate, ethyl lactate, and tetrahydrofurfuryl polyethylene glycol ether is preferred.

The drug sustained-release agent may be soybean oil, and may also be selected from sesame oil, sunflower seed oil, peanut oil, castor oil, corn oil, rapeseed oil, olive oil, cottonseed oil or other natural vegetable oil, or semi-natural fat artificially modified from natural vegetable oil (e.g., hydrogenated castor oil), purified fat and corresponding derivatives.

The drug sustained-release agent may also be selected from artificially synthesized fat including medium chain triglyceride with a carbon chain length of $C_6$-$C_{12}$ (e.g., one or a mixture of caprylic triglyceride and capric triglyceride), long chain triglyceride with a carbon chain length of $C_{14}$-$C_{24}$, glyceryl triacetate or other corresponding derivatives, ethyl oleate, white oil, dimethyl silicone oil, and animal fat having a low melting point.

The drug sustained-release agent may also be one or a mixture of two or more of natural vegetable oil, artificially modified semi-natural vegetable fat, purified fat, artificially synthesized fat, and animal fat having a low melting point.

Among others, the drug sustained-release agent is preferably soybean oil, and also preferably one or a mixture of two or more of ethyl oleate, castor oil, sesame oil and peanut oil, and most preferably one or a mixture of two or more of soybean oil, ethyl oleate, and castor oil.

If the drug sustained-release formulation is for local injection use, the corresponding menstruum and sustained-release agent are required to be non-stimulating (or weakly stimulating) and subjected to refinement, bacteria and pyrogen removal and the like.

With reference to the Examples (the Formulation and Animal Experiments sections), part of the preferred drug delivery systems according to the present invention, consisting of anesthetic analgesics and pharmaceutical adjuvants, is exemplified, wherein the anesthetic analgesics are at a concentration of 30-50 mg/ml (w/v) and the adjuvants consist of drug menstruum in a proportion of 10%-40% (v/v) and a sustained-release agent in a proportion of 60%-90% (v/v).

Therein, the drug menstruum is selected from benzyl alcohol, benzyl benzoate, and anhydrous ethanol.

Therein, the drug sustained-release agent is selected from soybean oil, ethyl oleate, and castor oil.

Another objective of the present invention is to provide a preparation method for non-addictive anesthetic analgesic sustained-release drug delivery systems.

The preparation method for non-addictive anesthetic analgesic sustained-release drug delivery systems comprises the following steps:

A. stock solution preparation: a certain amount of one or a mixture of two or more of the anesthetic analgesic is accurately weighed and dissolved in a volume of a drug menstruum, subjected to sonication or vortexing until the drug is completely dissolved; a prescribed amount of one or a mixture of two or more of a sustained-release agent is added, and sonicated or vortexed to prepare the desired stock solution of the drug delivery system;

B. sterile packing: under sterile conditions, the prepared drug solution is filtered through a film to remove impurities and bacteria, separated and packed into containers such as a penicillin bottle or an ampule, a Tillable injector, or a spray bottle, or an aerosol bottle (in the case of an aerosol bottle, the stock solution must be added first, and the bottle is then charged with a propellant and sealed), plugged with a stopper and sealed with a cover to obtain an analgesic sustained-release drug delivery system.

The prescribed composition according to the present invention may be prepared into various dosage forms.

The prescribed composition according to the present invention may be prepared into the following dosage forms: a formulation for injection, a spray, an aerosol, an ointment, a cream, a film, or a paste, preferably a formulation for injection, a spray, a film, or an aerosol, and most preferably a formulation for injection.

For the sustained-release drug delivery system according to the present invention, the drug carrier may be a penicillin bottle, an ampule, a fillable injector, a spray bottle, or an aerosol bottle.

The implementation methods of the non-addictive local anesthetic analgesic sustained-release drug delivery system according to the present invention are: analgesia by injection at nerve nodes near wound or at nerve root; analgesia by single- or multi-site intramuscular injection, single- or multi-site subcutaneous injection, application or spray infiltration at incision; and also analgesia through continuous or intermittent sustained-administration by means of automatic, semi-automatic, or manual infusion pumps.

Yet another objective of the present invention is to demonstrate the clinical use of the drug delivery system according to the present invention in the preparation of local analgesic medicaments.

Still another objective of the present invention is to demonstrate the clinical use of the drug delivery system, which is primarily used for providing anesthetic analgesia at post-operative wounds, as well as for anesthetic analgesia at site of wound from mechanical injuries such as cut, scratch, or puncture, scald wound, or burn wound; for anesthetic analgesia at site of wound from combat trauma caused by bullets, explosion, gunpowder, or chemicals; for anesthetic analgesia at local inflammatory lesion sites in the body caused by diseases such as herpes zoster, prosoponeuralgia, prosopalgia, arthralgia, muscle pain, or external hemorrhoid; and for anesthetic analgesia against local pain in the body caused by cancer.

The non-addictive anesthetic analgesic sustained-release drug delivery system according to the present invention (preferably illustrated with ropivacaine) is characteristic in the following aspects:

1. In the present invention, ropivacaine is used as a principle agent, for the first time, in preparation of an anesthetic analgesic sustained-release drug delivery system, and the major feature of such product lies in that, as compared to opioid drugs, it is non-addictive, sustained-released, useful for local anesthetic analgesia at body wound site or other pain sites, particularly local anesthetic analgesia at post-operative wounds, with the route of administration by single- or multi-site intramuscular injection or single- or multi-site subcutaneous injection at wound. Currently, there is no such product on the market domestically or aboard as a sustained-release drug delivery system prepared from the above drugs for post-operative anesthetic analgesia.

2. In the present invention, refined natural vegetable oil or artificially synthesized fat as oily sustained-release agent (natural vegetable oils such as soybean oil, peanut oil, sesame oil, and castor oil are conventional adjuvants for vaccine, contraceptive, and body vitamin supplementing formulation for injection) is used for the first time in the field of analgesia at wounds such as post-operative wounds, inflammatory wounds, mechanical injury wounds, burn wounds and combat wounds.

3. It is proposed in the present invention that a mixture of any one of benzyl alcohol, benzyl benzoate, and ethyl oleate together with ethanol is greatly miscible with one of soybean oil, sesame oil, and corn oil, and these are used in the drug delivery system for the prescribed composition according to the present invention.

4. It is discovered in the present invention that a mixed solvent formed from one, two or three of benzyl benzoate, benzyl alcohol, and ethanol, as compared to a single solvent, can substantially improve the drug loading of the drug delivery system and has excellent mutual solubilization (in the experimental examples, the drugs selected are ropivacaine free base, ropivacaine methanesulfonate, and ropivacaine hydrochloride).

5. In the experimental examples, sustained-release formulations are prepared with ropivacaine as the principle agent, and results of animal experiments (rat plantar hotplate stimulation method, post-op pain model Von Frey needle mechanic pain assay) demonstrate that a measurable duration of nerve block with a regular ropivacaine injection solution (methanesulfonate or hydrochloride salt) is about 2 hours (literatures indicate an analgesic duration for human of about 6-8 hours) while the sustained-release drug delivery system (drugs selected are ropivacaine free base or methanesulfonate) acts fast and has a notably extended duration of action.

6. The preferred active agent ropivacaine in the drug delivery system according to the present invention plays a role in local vasoconstriction, and when given locally, it may reduce wound bleeding and accelerate detumescence and healing of wound.

7. The active agent ropivacaine used in the drug delivery system according to the present invention plays a role in local vasoconstriction, and when given locally, it may reduce the dosage of the drug entering blood circulatory system through blood vessels, partially decrease cardiac toxicity and neural toxicity of the drug, and have much less clinical side effects as compared to central analgesics.

8. Currently in clinical practice, constant intravenous or epidural infusion of drugs with analgesia pumps is primarily used for analgesia in post-operative patients; whereas, in the present invention, local administration such as wound proximal intramuscular injection, wound infiltration, and ganglion region injection is used clinically, and therefore the product of the present invention may be used conveniently with higher safety.

9. The preferred ropivacaine sustained-release drug delivery system according to the present invention may be prepared into various dosages forms for use, in addition to its use in post-op local anesthetic analgesia, in analgesic treatment against neuropathic pain induced by herpes zoster, pathological changes, or medicaments, prosoponeuralgia, prosopalgia, arthralgia, muscle pain, internal and external haemorrhoid inflammatory pain, pain resulted from cancer, wound pain from mechanical injuries such as cut, scratch, and puncture, scald wound pain, burn wound pain, as well as pain from combat trauma caused by bullets, explosion, gunpowder, or chemicals, and the various dosage forms may be injected, smeared, sprayed and so on.

10. When the local anesthetic analgesic sustained-release formulation prepared from the ropivacaine free base as the most preferred principle agent according to the present invention is used for local anesthetic analgesia, due to the characteristic of ropivacaine of discriminating motor nerves from sensory nerves, motor nerve blocking tends to be lessened, and patients regain motion faster.

DETAILED DESCRIPTION OF VARIOUS EMBODIMENTS

Figure 1:
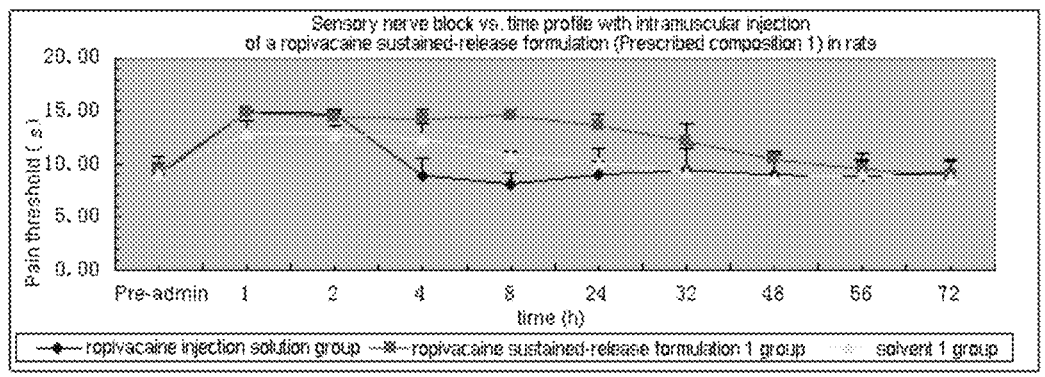
FIG. 1: Sensory nerve block vs. time profile with intramuscular injection of a ropivacaine sustained-release formulation (Prescribed composition 1) in rats
Figure 2:
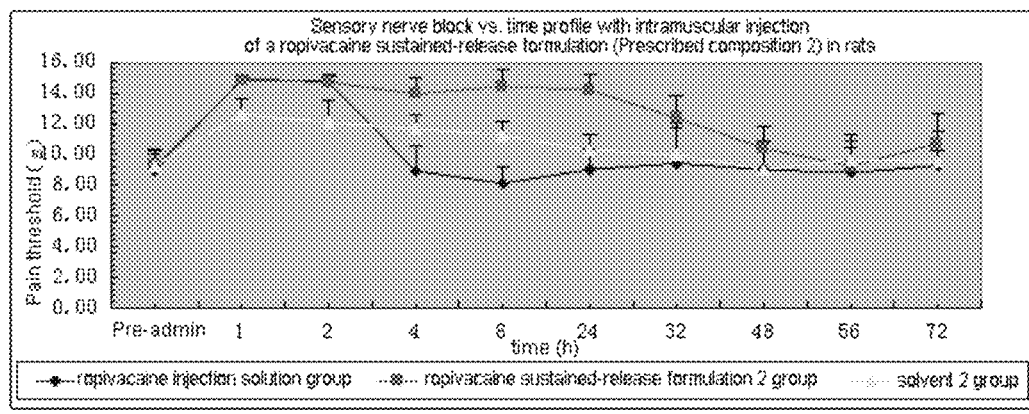
FIG. 2: Sensory nerve block vs. time profile with intramuscular injection of a ropivacaine sustained-release formulation (Prescribed composition 2) in rats
Figure 3:
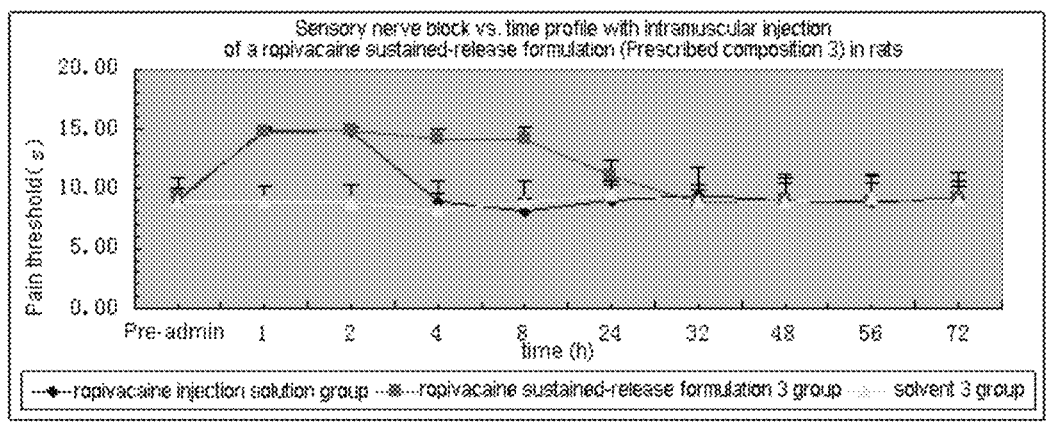
FIG. 3: Sensory nerve block vs. time profile with intramuscular injection of a ropivacaine sustained-release formulation (Prescribed composition 3) in rats
Figure 4:
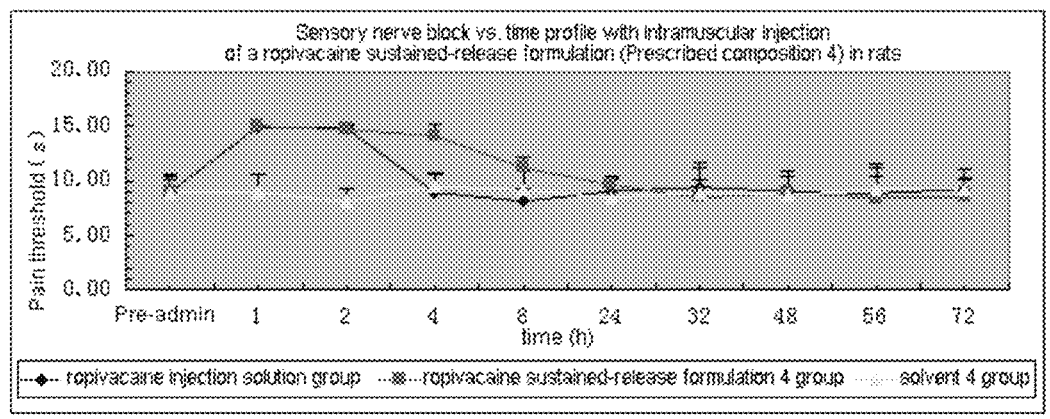
FIG. 4: Sensory nerve block vs. time profile with intramuscular injection of a ropivacaine sustained-release formulation (Prescribed composition 4) in rats
Figure 5:
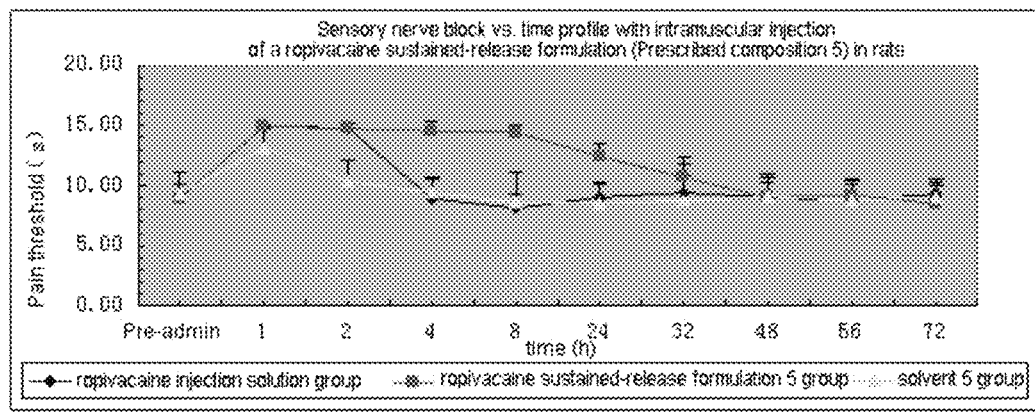
FIG. 5: Sensory nerve block vs. time profile with intramuscular injection of a ropivacaine sustained-release formulation (Prescribed composition 5) in rats
Figure 6:
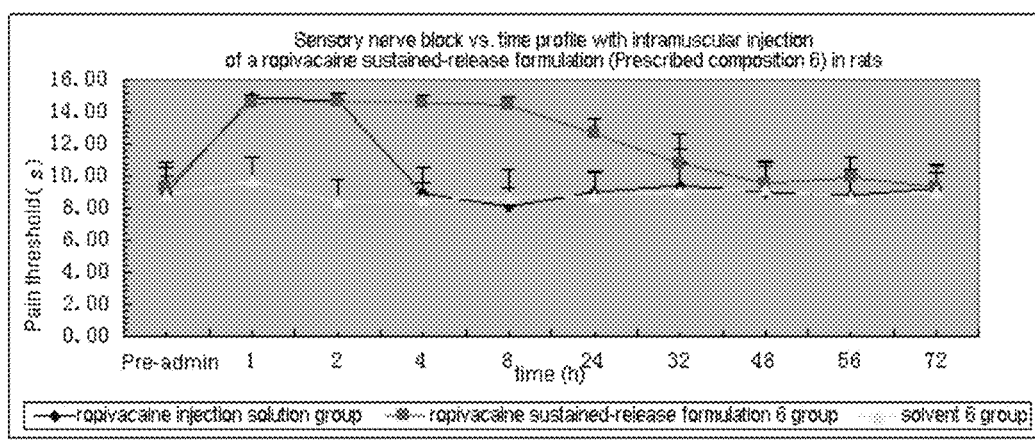
FIG. 6: Sensory nerve block vs. time profile with intramuscular injection of a ropivacaine sustained-release formulation (Prescribed composition 6) in rats
Figure 7:
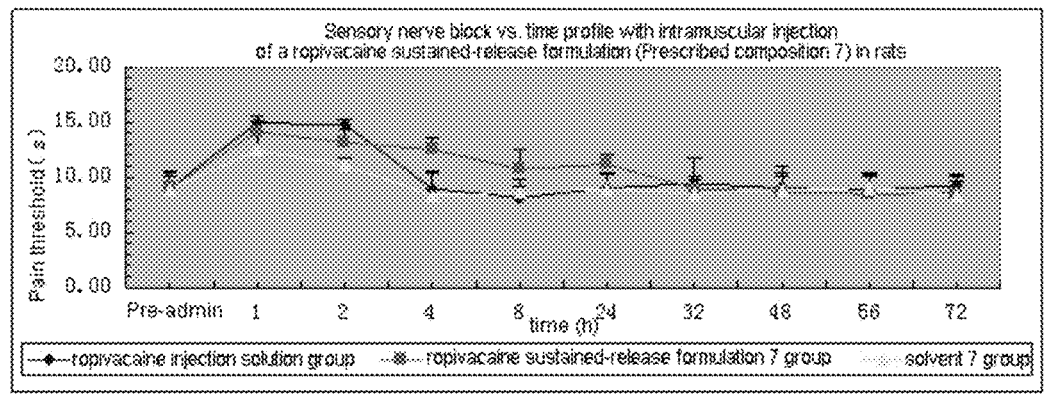
FIG. 7: Sensory nerve block vs. time profile with intramuscular injection of a ropivacaine sustained-release formulation (Prescribed composition 7) in rats
Figure 8:
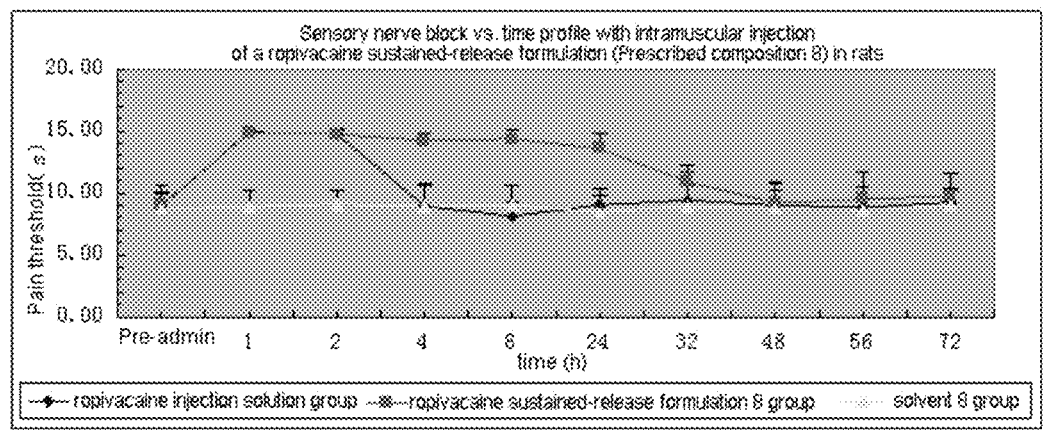
FIG. 8: Sensory nerve block vs. time profile with intramuscular injection of a ropivacaine sustained-release formulation (Prescribed composition 8) in rats

The prescribed composition, preparation method, and use according to the present invention are further illustrated with reference to the following experimental examples and implementing examples to which the scope of the present invention is not limited.

Experimental Example 1

Solubility Tests of Ropivacaine Free Base and Corresponding Salts

Ropivacaine free base and salts thereof (methanesulfonate and hydrochloride) raw drugs were each accurately weighed, into which 1 ml each of anhydrous ethanol, benzyl alcohol, glyceryl monoacetate, benzyl benzoate, ethyl lactate, sesame oil, soybean oil, ethyl oleate, corn oil, castor oil, olive oil, and tetrahydrofurfuryl polyethylene glycol ether were added respectively, and the dissolution process was observed. If a drug dissolved completely, addition of this drug was continued until saturation. Ranges of solubility of the drugs in various solvents were preliminarily determined, as shown in the table below.

TABLE 2

Solubility of ropivacaine and corresponding salts in various solvents (in part) (25° C.)

| Menstruum name | Solubility (mg/ml) | | |
|---|---|---|---|
| | Ropivacaine free base | Ropivacaine methansulfonate | Ropivacaine hydrochloride |
| anhydrous ethanol | 155 | 320 | 95 |
| benzyl alcohol | 225 | 550 | 140 |
| glyceryl monoacetate | 18 | 50 | 30 |
| benzyl benzoate | 70 | 2 | 2.5 |
| ethyl lactate | 80 | 198 | 16.5 |
| Soybean oil | 9.6 | 2.5 | 2 |
| Sesame oil | 11.7 | 1.7 | 2 |
| ethyl oleate | 14.9 | 2 | 2.2 |
| Corn oil | 9.4 | 1.7 | 2.5 |
| castor oil | 17 | 2 | 1.7 |
| Olive oil | 9.8 | 2 | 1.7 |
| tetrahydrofurfuryl polyethylene glycol ether | 39.6 | 13.2 | 9 |

Experimental results demonstrated that: at ambient temperature (25° C.), ropivacaine free base had superior solubility in anhydrous ethanol and benzyl alcohol, each exceeding 150 mg/ml, with less superior solubility in benzyl benzoate, ethyl lactate, and tetrahydrofurfuryl polyethylene glycol ether; ropivacaine methansulfonate had superior solubility in anhydrous ethanol, benzyl alcohol, and ethyl lactate, each exceeding 190 mg/ml, with less superior solubility in glyceryl monoacetate; ropivacaine hydrochloride had superior solubility in benzyl alcohol of more than 100 mg/ml, with less superior solubility in anhydrous ethanol, glyceryl monoacetate, and ethyl lactate. Therefore, four solvents, anhydrous ethanol, benzyl alcohol, benzyl benzoate, and ethyl lactate, may be the choices for the drug menstruum while glyceryl monoacetate and tetrahydrofurfuryl polyethylene glycol ether may be the second choices, among which anhydrous ethanol and benzyl alcohol are preferred.

Experimental Example 2

Preliminary Screening Experiments for Drug Delivery Systems (in Part) in the Sustained-Release Formulation Drug Delivery System Anhydrous ethanol, benzyl alcohol, ethyl lactate, benzyl benzoate, glyceryl monoacetate, and tetrahydrofurfuryl polyethylene glycol ether were used as drug menstruum and mixed miscible with ethyl oleate, glyceryl triacetate, castor oil, soybean oil, corn oil, sesame oil, and medium chain triglyceride respectively. White oil and hydrogenated castor oil was optionally added into some of the mixed solvents. Miscible dissolution was observed.

Part of the preferable drug delivery system is shown below:
benzyl alcohol/ethyl oleate
benzyl alcohol/tetrahydrofurfuryl polyethylene glycol ether
benzyl alcohol/glyceryl triacetate
benzyl alcohol/soybean oil
benzyl alcohol/sesame oil
benzyl alcohol/corn oil
benzyl alcohol/castor oil
benzyl alcohol/medium chain triglyceride
anhydrous ethanol/ethyl oleate
anhydrous ethanol/tetrahydrofurfuryl polyethylene glycol ether
anhydrous ethanol/benzyl benzoate
anhydrous ethanol/glyceryl triacetate
anhydrous ethanol/castor oil
anhydrous ethanol/ethyl oleate/soybean oil
anhydrous ethanol/benzyl benzoate/glyceryl triacetate
anhydrous ethanol/benzyl benzoate/soybean oil
anhydrous ethanol/benzyl benzoate/castor oil
anhydrous ethanol/benzyl benzoate/castor oil/hydrogenated castor oil
anhydrous ethanol/benzyl benzoate/corn oil
anhydrous ethanol/benzyl benzoate/tetrahydrofurfuryl polyethylene glycol ether
anhydrous ethanol/benzyl benzoate/sesame oil
anhydrous ethanol/benzyl benzoate/medium chain triglyceride
benzyl alcohol/benzyl benzoate/ethyl oleate
benzyl alcohol/benzyl benzoate/tetrahydrofurfuryl polyethylene glycol ether
benzyl alcohol/benzyl benzoate/glyceryl triacetate
benzyl alcohol/benzyl benzoate/castor oil/hydrogenated castor oil benzyl alcohol/benzyl benzoate/soybean oil
benzyl alcohol/benzyl benzoate/soybean oil/white oil
benzyl alcohol/benzyl benzoate/medium chain triglyceride
benzyl alcohol/ethyl oleate/soybean oil
benzyl alcohol/ethyl oleate/soybean oil/white oil
anhydrous ethanol/glyceryl monoacetate/tetrahydrofurfuryl polyethylene glycol ether
anhydrous ethanol/glyceryl monoacetate/glyceryl triacetate
benzyl alcohol/glyceryl monoacetate/tetrahydrofurfuryl polyethylene glycol ether
benzyl alcohol/glyceryl monoacetate/glyceryl triacetate
benzyl alcohol/glyceryl monoacetate/benzyl benzoate
anhydrous ethanol/ethyl lactate/ethyl oleate
anhydrous ethanol/ethyl lactate/tetrahydrofurfuryl polyethylene glycol ether
anhydrous ethanol/ethyl lactate/glyceryl triacetate
anhydrous ethanol/ethyl lactate/benzyl benzoate
anhydrous ethanol/ethyl lactate/castor oil
benzyl alcohol/ethyl lactate/ethyl oleate
benzyl alcohol/ethyl lactate/glyceryl triacetate
benzyl alcohol/ethyl lactate/tetrahydrofurfuryl polyethylene glycol ether
benzyl alcohol/ethyl lactate/corn oil
benzyl alcohol/ethyl lactate/sesame oil
benzyl alcohol/ethyl lactate/soybean oil
benzyl alcohol/ethyl lactate/castor oil
benzyl alcohol/ethyl lactate/benzyl benzoate
benzyl alcohol/ethyl lactate/medium chain triglyceride
benzyl alcohol/anhydrous ethanol/castor oil/hydrogenated castor oil
benzyl alcohol/anhydrous ethanol/ethyl oleate
benzyl alcohol/anhydrous ethanol/soybean oil/white oil
benzyl alcohol/anhydrous ethanol/corn oil
benzyl alcohol/anhydrous ethanol/glyceryl triacetate
benzyl alcohol/anhydrous ethanol/sesame oil
benzyl alcohol/anhydrous ethanol/medium chain triglyceride The results suggested that: the mixture of ethanol and any one of benzyl alcohol, benzyl benzoate, and ethyl oleate showed excellent miscibility with one of soybean oil, sesame oil, and corn oil, whereas ethanol alone did not mix miscibly with one of soybean oil, sesame oil, and corn oil; castor oil might be mixed with any one of ethanol, benzyl alcohol, and benzyl benzoate.

Experimental Example 3

Formulation Experiment for Sustained-Release Formulation Delivery System (in Part)

A certain amount of bupivacaine free base, bupivacaine hydrochloride, ropivacaine free base, ropivacaine methanesulfonate, ropivacaine hydrochloride, dezocine (an opioid analgesic), and parecoxib (a selective COX-2 inhibitor), were weighed respectively, into each of which was added drug menstruum and drug sustained-release agents, and the stabilization process of the formulations was observed. Detailed experimental procedures were similar to those in Experimental Example 2. As shown in the experimental results, part of the drug delivery system combinations that may be used in the formula of the sustained-release formulation delivery system is as follows:
benzyl alcohol/ethyl oleate
benzyl alcohol/glyceryl triacetate
benzyl alcohol/soybean oil
benzyl alcohol/castor oil
benzyl alcohol/sesame oil
benzyl alcohol/corn oil
benzyl alcohol/medium chain triglyceride
anhydrous ethanol/ethyl oleate
anhydrous ethanol/benzyl benzoate
anhydrous ethanol/glyceryl triacetate
anhydrous ethanol/castor oil
anhydrous ethanol/ethyl oleate/soybean oil
anhydrous ethanol/ethyl oleate/corn oil
anhydrous ethanol/ethyl oleate/sesame oil
anhydrous ethanol/benzyl benzoate/glyceryl triacetate
anhydrous ethanol/benzyl benzoate/soybean oil
anhydrous ethanol/benzyl benzoate/castor oil
anhydrous ethanol/benzyl benzoate/castor oil/hydrogenated castor oil
anhydrous ethanol/benzyl benzoate/corn oil
anhydrous ethanol/benzyl benzoate/tetrahydrofurfuryl polyethylene glycol ether
anhydrous ethanol/benzyl benzoate/sesame oil
anhydrous ethanol/benzyl benzoate/medium chain triglyceride
benzyl alcohol/benzyl benzoate/ethyl oleate
benzyl alcohol/benzyl benzoate/tetrahydrofurfuryl polyethylene glycol ether
benzyl alcohol/benzyl benzoate/glyceryl triacetate
benzyl alcohol/benzyl benzoate/castor oil
benzyl alcohol/benzyl benzoate/soybean oil
benzyl alcohol/benzyl benzoate/soybean oil/white oil
benzyl alcohol/benzyl benzoate/medium chain triglyceride
anhydrous ethanol/glyceryl monoacetate/glyceryl triacetate
benzyl alcohol/glyceryl monoacetate/glyceryl triacetate
benzyl alcohol/glyceryl monoacetate/benzyl benzoate
anhydrous ethanol/ethyl lactate/ethyl oleate
anhydrous ethanol/ethyl lactate/glyceryl triacetate
anhydrous ethanol/ethyl lactate/benzyl benzoate
anhydrous ethanol/ethyl lactate/castor oil
benzyl alcohol/ethyl lactate/ethyl oleate
benzyl alcohol/ethyl lactate/corn oil
benzyl alcohol/ethyl lactate/sesame oil
benzyl alcohol/ethyl lactate/soybean oil
benzyl alcohol/ethyl lactate/castor oil
benzyl alcohol/ethyl lactate/benzyl benzoate
benzyl alcohol/ethyl lactate/medium chain triglyceride
benzyl alcohol/anhydrous ethanol/castor oil
benzyl alcohol/anhydrous ethanol/castor oil/hydrogenated castor oil
benzyl alcohol/anhydrous ethanol/ethyl oleate
benzyl alcohol/anhydrous ethanol/soybean oil
benzyl alcohol/anhydrous ethanol/corn oil
benzyl alcohol/anhydrous ethanol/glyceryl triacetate
benzyl alcohol/anhydrous ethanol/sesame oil
benzyl alcohol/anhydrous ethanol/medium chain triglyceride The experimental results suggested that ropivacaine free base, ropivacaine methanesulfonate, and ropivacaine hydrochloride showed an increased solubility in the mixture of benzyl benzoate with one of ethanol and benzyl alcohol, while dezocine and parecoxib had good solubility in ethanol, benzyl alcohol, benzyl benzoate, and ethyl lactate.

Experimental Example 4

Verification of the Solubility of Various Local Anesthetics in the Sustained-Release Drug Delivery System With reference to the results in Experimental Examples 2 and 3, drug delivery systems of benzyl alcohol/benzyl benzoate/castor oil, benzyl alcohol/ethyl oleate/castor oil, benzyl alcohol/benzyl benzoate/soybean oil, benzyl alcohol/ethyl oleate/soybean oil, ethanol/benzyl benzoate/castor oil, ethanol/ethyl oleate/castor oil, ethanol/benzyl benzoate/soybean oil, benzyl alcohol/medium chain triglyceride, ethyl oleate/soybean oil were used as examples for verification of the solubility of various local anesthetics in the sustained-release drug delivery system, which local anesthetics were selected from procaine free base, procaine hydrochloride, lidocaine free base, lidocaine hydrochloride, bupivacaine free base, bupivacaine hydrochloride, tetracaine free base, tetracaine hydrochloride, dibucaine free base, dibucaine hydrochloride, Articaine free base, and Articaine hydrochloride (12 in total). The 12 local anesthetics were each added into the selected drug delivery systems, and the dissolution process of the drugs was observed (norm: 15-20 mg/ml, observed at 25° C. for 24 hours with recordation; or observed at 4° C. for 24 hours with recordation).

As shown in the results, all 12 local anesthetics were well dissolved in the various chosen drug delivery systems; at 4° C., the 12 local anesthetics had good solubility in benzyl alcohol/benzyl benzoate/castor oil, benzyl alcohol/ethyl oleate/castor oil, benzyl alcohol/benzyl benzoate/soybean oil, benzyl alcohol/ethyl oleate/soybean oil, ethanol/benzyl benzoate/castor oil, ethanol/ethyl oleate/castor oil, ethanol/benzyl benzoate/soybean oil, and benzyl alcohol/medium chain oil, and the formulations were clear; procaine and tetracaine slightly precipitated in the ethyl oleate/soybean oil drug delivery system, while the other local anesthetics showed good solubility in the ethyl oleate/soybean oil drug delivery system.

Experimental Example 5

Experiments on In Vitro Stability of the Drug Formulations

On the basis of the empirical prescribed composition of the ropivacaine free base and ropivacaine methanesulfonate delivery systems selected in Experimental Example 3, benzyl alcohol/ethyl oleate, anhydrous ethanol/ethyl oleate, benzyl alcohol/anhydrous ethanol/ethyl oleate, benzyl alcohol/castor oil, benzyl alcohol/soybean oil, benzyl alcohol/benzyl benzoate/soybean oil, anhydrous ethanol/benzyl benzoate/soybean oil, anhydrous ethanol/ethyl oleate/soybean oil, anhydrous ethanol/castor oil, benzyl alcohol/ethyl oleate/soybean oil, anhydrous ethanol/ethyl oleate/castor oil, benzyl alcohol/benzyl benzoate/castor oil, anhydrous ethanol/benzyl benzoate/castor oil, benzyl alcohol/benzyl benzoate/ethyl oleate, benzyl alcohol/benzyl benzoate/ethyl oleate/soybean oil were selected for prescription. A certain amount of ropivacaine methanesulfonate or ropivacaine free base was dissolved into each of the above, left to stand at room temperature for 24 h, and dissolution stability thereof was observed and recorded; or left to stand at 4° C. for 24 h, and dissolution stability thereof was observed and recorded.

TABLE III

Test results on dissolution stability of ropivacaine sustained-release formulations at various concentrations

| Prescribed composition | Incorporated drug | Concentration (mg/ml) | Ambient temperature (25° C.) | Low temperature (4° C.) |
| --- | --- | --- | --- | --- |
| Benzyl alcohol (10%)/ethyl oleate (90%) | Ropivacaine free base | 30 | Clear | Clear |
| Benzyl alcohol (10%)/ethyl oleate (90%) | Ropivacaine free base | 35 | Clear | Extremely trivial precipitation |
| Benzyl alcohol (10%)/ethyl oleate (90%) | Ropivacaine free base | 40 | Clear | Trivial precipitation |
| Anhydrous ethanol (10%)/ethyl oleate (90%) | Ropivacaine free base | 25 | Clear | Clear |
| Anhydrous ethanol (10%)/ethyl oleate (90%) | Ropivacaine free base | 30 | Clear | Trivial precipitation |
| Anhydrous ethanol (10%)/ethyl oleate (90%) | Ropivacaine free base | 35 | Clear | Small amount of precipitation |
| Benzyl alcohol (8%)/anhydrous ethanol (8%)/ethyl oleate (84%) | Ropivacaine free base | 40 | Clear | Clear |
| Benzyl alcohol (8%)/anhydrous ethanol (8%)/ethyl oleate (84%) | Ropivacaine free base | 45 | Clear | Clear |
| Benzyl alcohol (8%)/anhydrous ethanol (8%)/ethyl oleate (84%) | Ropivacaine free base | 50 | Clear | Trivial precipitation |
| Benzyl alcohol (10%)/castor oil (90%) | Ropivacaine free base | 35 | Clear | Clear |
| Benzyl alcohol (10%)/castor oil (90%) | Ropivacaine free base | 40 | Clear | Clear |
| Benzyl alcohol (10%)/castor oil (90%) | Ropivacaine free base | 45 | Clear | Trivial precipitation |
| Benzyl alcohol (10%)/soybean oil (90%) | Ropivacaine free base | 25 | Clear | Clear |
| Benzyl alcohol (10%)/soybean oil (90%) | Ropivacaine free base | 30 | Clear | Extremely trivial precipitation |
| Benzyl alcohol (10%)/soybean oil (90%) | Ropivacaine free base | 35 | Clear | Trivial precipitation |
| Anhydrous ethanol (10%)/castor oil (90%) | Ropivacaine free base | 25 | Clear | Clear |
| Anhydrous ethanol (10%)/castor oil (90%) | Ropivacaine free base | 30 | Clear | Trivial precipitation |
| Anhydrous ethanol (10%)/castor oil (90%) | Ropivacaine free base | 35 | Clear | Trivial precipitation |
| Benzyl alcohol (10%)/ethyl oleate (30%)/soybean oil (60%) | Ropivacaine free base | 30 | Clear | Clear |
| Benzyl alcohol (10%)/ethyl oleate (30%)/soybean oil (60%) | Ropivacaine free base | 35 | Clear | Extremely trivial precipitation |
| Benzyl alcohol (10%)/ethyl oleate (30%)/soybean oil (60%) | Ropivacaine free base | 40 | Clear | Trivial precipitation |
| Benzyl alcohol (10%)/benzyl benzoate (30%)/soybean oil (60%) | Ropivacaine free base | 35 | Clear | Clear |

TABLE III-continued

Test results on dissolution stability of ropivacaine sustained-release formulations at various concentrations

| Prescribed composition | Incorporated drug | Concentration (mg/ml) | Ambient temperature (25° C.) | Low temperature (4° C.) |
| --- | --- | --- | --- | --- |
| Benzyl alcohol (10%)/benzyl benzoate (30%)/soybean oil (60%) | Ropivacaine free base | 40 | Clear | Clear |
| Benzyl alcohol (10%)/benzyl benzoate (30%)/soybean oil (60%) | Ropivacaine free base | 45 | Clear | Extremely trivial precipitation |
| Anhydrous ethanol (10%)/benzyl benzoate (30%)/soybean oil (60%) | Ropivacaine free base | 30 | Clear | Clear |
| Anhydrous ethanol (10%)/benzyl benzoate (30%)/soybean oil (60%) | Ropivacaine free base | 35 | Clear | Trivial precipitation |
| Anhydrous ethanol (10%)/benzyl benzoate (30%)/soybean oil (60%) | Ropivacaine free base | 40 | Clear | precipitation |
| Anhydrous ethanol (10%)/ethyl oleate (30%)/soybean oil (60%) | Ropivacaine free base | 25 | Clear | Clear |
| Anhydrous ethanol (10%)/ethyl oleate (30%)/soybean oil (60%) | Ropivacaine free base | 30 | Clear | Trivial precipitation |
| Anhydrous ethanol (10%)/ethyl oleate (30%)/soybean oil (60%) | Ropivacaine free base | 35 | Clear | precipitation |
| Anhydrous ethanol (10%)/ethyl oleate (30%)/castor oil (60%) | Ropivacaine free base | 25 | Clear | Clear |
| Anhydrous ethanol (10%)/ethyl oleate (30%)/castor oil (60%) | Ropivacaine free base | 30 | Clear | Clear |
| Anhydrous ethanol (10%)/ethyl oleate (30%)/castor oil (60%) | Ropivacaine free base | 35 | Clear | Trivial precipitation |
| Benzyl alcohol (10%)/benzyl benzoate (15%)/castor oil (75%) | Ropivacaine free base | 40 | Clear | Clear |
| Benzyl alcohol (10%)/benzyl benzoate (15%)/castor oil (75%) | Ropivacaine free base | 45 | Clear | Clear |
| Benzyl alcohol (10%)/benzyl benzoate (15%)/castor oil (75%) | Ropivacaine free base | 50 | Clear | Extremely trivial precipitation |
| Anhydrous ethanol (10%)/benzyl benzoate (15%)/castor oil (75%) | Ropivacaine free base | 30 | Clear | Clear |
| Anhydrous ethanol (10%)/benzyl benzoate (15%)/castor oil (75%) | Ropivacaine free base | 35 | Clear | Clear |
| Anhydrous ethanol (10%)/benzyl benzoate (15%)/castor oil (75%) | Ropivacaine free base | 40 | Clear | Clear |
| Benzyl alcohol (10%)/benzyl benzoate (30%)/ethyl oleate (60%) | Ropivacaine free base | 35 | Clear | Clear |
| Benzyl alcohol (8%)/benzyl benzoate (42%)/ethyl oleate (50%) | Ropivacaine free base | 35 | Clear | Extremely trivial precipitation |
| Benzyl alcohol (10%)/benzyl benzoate (30%)/ethyl oleate (30%) Soybean oil (30%) | Ropivacaine free base | 35 | Clear | Clear |
| Benzyl alcohol (8%)/benzyl benzoate (42%)/ethyl oleate (25%) Soybean oil (25%) | Ropivacaine free base | 35 | Clear | Extremely trivial precipitation |
| Benzyl alcohol (12%)/ethyl oleate (88%) | Ropivacaine methanesulfonate | 12 | Clear | Trivial precipitation |
| Benzyl alcohol (14%)/ethyl oleate (86%) | Ropivacaine methanesulfonate | 12 | Clear | Trivial precipitation |
| Benzyl alcohol (16%)/ethyl oleate (84%) | Ropivacaine methanesulfonate | 12 | Clear | Clear |
| Anhydrous ethanol (16%)/ethyl oleate (84%) | Ropivacaine methanesulfonate | 12 | Clear | Trivial precipitation |
| Anhydrous ethanol (18%)/ethyl oleate (82%) | Ropivacaine methanesulfonate | 12 | Clear | Clear |
| Anhydrous ethanol (20%)/ethyl oleate (80%) | Ropivacaine methanesulfonate | 12 | Clear | Clear |
| Benzyl alcohol (6%)/anhydrous ethanol (6%)/ethyl oleate (84%) | Ropivacaine methanesulfonate | 12 | Clear | Clear |
| Benzyl alcohol (8%)/anhydrous ethanol (8%)/ethyl oleate (84%) | Ropivacaine methanesulfonate | 12 | Clear | Clear |
| Benzyl alcohol (10%)/anhydrous ethanol (10%)/ethyl oleate (84%) | Ropivacaine methanesulfonate | 12 | Clear | Trivial precipitation |

As shown in the experimental results, at different temperature, the maximum concentration of ropivacaine free base in the prescribed composition 1 [benzyl alcohol (8%)/anhydrous ethanol (8%)/ethyl oleate (84%)], composition 2 [benzyl alcohol (10%)/castor oil (90%)], composition 3 [benzyl alcohol (10%)/ethyl oleate (30%)/soybean oil (60%)], composition 4 [benzyl alcohol (10%)/benzyl benzoate (30%)/soybean oil (60%)], composition 5 [benzyl alcohol (10%)/benzyl benzoate (15%)/castor oil (75%)], composition 6 [anhydrous ethanol (10%)/benzyl benzoate (15%)/castor oil (75%)], composition 7 [benzyl alcohol (10%)/benzyl benzoate (30%)/ethyl oleate (60%)], composition 8 [benzyl alcohol (8%)/benzyl benzoate (42%)/ethyl oleate (50%)], composition 9 [benzyl alcohol (10%)/benzyl benzoate (30%)/ethyl oleate (30%)/soybean oil (30%)], and composition 10 [benzyl alcohol (8%)/benzyl benzoate (42%)/ethyl oleate (25%)/soybean oil (25%)] was about 35 mg/ml; the maximum concentration of ropivacaine free base in the prescribed composition 11 [benzyl alcohol (10%)/ethyl oleate (90%)], 12, [benzyl alcohol (10%)/soybean oil (90%)], composition 13 [anhydrous ethanol (10%)/benzyl benzoate (30%)/soybean oil (60%)], and composition 14 [anhydrous ethanol (10%)/ethyl oleate (30%)/castor oil (60%)] was more than 30 mg/ml; meanwhile, the solubility of ropivacaine methanesulfonate in various prescribed compositions was slightly poorer than that of ropivacaine free base.

On condition that each sustained-release formulation was stably dissolved, the concentration of prescribed compositions having better ropivacaine free base solubility was measured. The general procedure was as follows: prescribed compositions having good solubility after storage at 4° C. for 24 h was left to stand for 30 days and observed, and those having better degree of clarity were screened for measurement of concentration. Detailed results are shown in the table below.

TABLE IV

Experimental results for structural stability of ropivacaine sustained-release formulations (content determination)

| No. | Prescribed composition | Incorporated drug | Concentration (mg/ml) | Measured concentration (mg/ml) |
|---|---|---|---|---|
| 1 | Benzyl alcohol (10%)/benzyl benzoate (15%)/soybean oil (75%) | Ropivacaine free base | 35 | 35.5 |
| 2 | Anhydrous ethanol (10%)/benzyl benzoate (15%)/soybean oil (75%) | Ropivacaine free base | 30 | 29.7 |
| 3 | Benzyl alcohol (8%)/anhydrous ethanol (8%)/ethyl oleate (84%) | Ropivacaine free base | 45 | 44.3 |
| 4 | Benzyl alcohol (10%)/castor oil (90%) | Ropivacaine free base | 40 | 41.2 |
| 5 | Benzyl alcohol (10%)/ethyl oleate (30%)/soybean oil (60%) | Ropivacaine free base | 30 | 30.2 |
| 6 | Benzyl alcohol (10%)/benzyl benzoate (15%)/castor oil (75%) | Ropivacaine free base | 45 | 45.9 |
| 7 | Anhydrous ethanol (10%)/benzyl benzoate (15%)/castor oil (75%) | Ropivacaine free base | 40 | 39.8 |
| 8 | Benzyl alcohol (10%)/soybean oil (90%) | Ropivacaine free base | 30 | 30.3 |

As shown in the experimental results, ropivacaine free base in various prescribed compositions was structurally stable and did not degrade.

Experimental Example 6

Preliminary Study on Compound Compositions of Non-Addictive Anesthetic Analgesic Sustained-Release Formulations On the basis of the prescribed compositions in Table IV, dezocine, an opioid analgesic, and parecoxib, a selective COX-2 inhibitor, were respectively incorporated into the drug delivery systems of the above prescribed compositions, and the formulation stability was observed at ambient temperature (25° C.) and low temperature (4° C.) (for a duration of about 24 h). Detailed results suggested that the solubility of parecoxib in the drug delivery systems was above 20 mg/ml (for a regular injection formulation, 40 mg/dose, 1 dose/6-12 h, daily dosage not more than 80 mg) while the solubility of dezocine in the drug delivery systems was above 30 mg/ml (for a regular injection formulation, 10 mg/dose, 1 dose/2-4 h, daily dosage not more than 120 mg). As such, a mixture of ropivacaine free base together with dezocine or parecoxib in such drug delivery systems may be used so as to formulate a sustained-release analgesic compound formulation having a synergistic analgesic effect (analgesics with different targets used in combination show certain synergistic effect).

Experimental Example 7

Effect in Wound Healing in Rats with Intramuscular Injection of Various Prescribed Compositions Experiment grouping and dosing regimen: about 65 male SD rats of 230-250 g were adaptively fed for 2-3 days, and then screened and divided into 10 groups with 6 rats in each group according to their weight. The groups were respectively: model control group, ropivacaine injection solution group, ropivacaine formulation-1 group, ropivacaine formulation-2 group, ropivacaine formulation-3 group, ropivacaine formulation-4 group, ropivacaine formulation-5 group, ropivacaine formulation-6 group, ropivacaine formulation-7 group, and ropivacaine formulation-8 group (see Table IV for detailed prescribed composition and specification). The model control group was injected with physiological saline, and ropivacaine injection solution group and ropivacaine formulations 1-8 groups were given at a dosage of 0.5 ml/rat.

Basic experimental procedures: after the test animals were screened and grouped according to their weight, hair on the back of the rats in each experimental groups were removed; on the next day, 2 cm*1 cm rat back full-thickness defect wound models were established upon operation, designated as D0, and photographs were recorded. The rats were randomly grouped, and administrated in groups by means of multi-site intramuscular injection at wound proximity.

Observation indicators: at different timepoints on D1, D3, D7, D14, and D21 after administration, healing of wounds in rats from each group was observed respectively, rated according to area of healed wounds and recovery state, and photographs were then recorded.

Results assessment: as shown in Table V, wound healing in rats in different groups and at various observation timepoints was comparatively assessed, and the results suggested that sustained-release ropivacaine formulations of different prescribed composition might not have substantially different impact on wound healing in rats.

TABLE V

Rating of wound healing in rats given ropivacaine formulations of different prescribed composition (n = 6)

| Groups | D 1 | D 3 | D 7 | D 14 | D 21 |
|---|---|---|---|---|---|
| Blank control group | — | 18.37% | 49.36% | 88.38% | 97.39% |
| Ropivacaine methanesulfonate injection solution group | — | 22.41% | 55.31% | 79.27% | 96.37% |
| Ropivacaine formulation 1 group | — | 19.32% | 61.97% | 89.26% | 98.13% |
| Ropivacaine formulation 2 group | — | 24.42% | 49.12% | 90.15% | 96.58% |
| Ropivacaine formulation 3 group | — | 28.18% | 57.30% | 93.27% | 94.96% |
| Ropivacaine formulation 4 group | — | 20.21% | 54.18% | 87.36% | 98.46% |
| Ropivacaine formulation 5 group | — | 22.87% | 57.26% | 81.25% | 99.15% |
| Ropivacaine formulation 6 group | — | 19.90% | 51.74% | 78.54% | 96.33% |

TABLE V-continued

Rating of wound healing in rats given ropivacaine formulations of different prescribed composition (n = 6)

| Groups | D 1 | D 3 | D 7 | D 14 | D 21 |
|---|---|---|---|---|---|
| Ropivacaine formulation 7 group | — | 23.45% | 62.57% | 85.42% | 99.37% |
| Ropivacaine formulation 8 group | — | 19.81% | 58.22% | 79.48% | 96.75% |

Experimental Example 8

Study on Efficacy of Ropivacaine Sustained-Release Formulations of Prescribed Compositions (Thermal Stimulation)

Experiment grouping and dosing regimen: about 110 male SD rats of 230-250 g were adaptively fed for 2-3 days, and then subjected to experiments. The rats were divided into 17 groups which were respectively: ropivacaine injection solution group, ropivacaine formulation-1 group, solvent 1 group, ropivacaine formulation-2 group, solvent 2 group, ropivacaine formulation-3 group, solvent 3 group, ropivacaine formulation-4 group, solvent 4 group, ropivacaine formulation-5 group, solvent 5 group, ropivacaine formulation-6 group, solvent 6 group, ropivacaine formulation-7 group, solvent 7 group, ropivacaine formulation-8 group, solvent 8 group (see Table IV for detailed prescribed composition and specification), with a dosage of 0.5 ml/rat for each group.

Details experimental procedures were as follows:

1. Sensory nerve blocking tests: 102 animals that had a response time of 6-8 s were screened and chosen from 110 male SD rats (the screening method is a thermal radiation method, see the Measurement section below for detailed procedures) and divided into 17 groups, as described in details in the previous paragraph. Each group was injected with ropivacaine methanesulfonate injection solution, ropivacaine sustained-release formulations of various prescribed compositions and corresponding blank solvents, with a dosage of 0.5 ml/rat. Detailed operation procedures were as below: the rats were anesthetized with an appropriate amount of diethyl ether; a needle was inserted at approximately ⅓ along the elongation of the right humeral motor, in the anteromedial direction with the end of the needle tilted up at 45°, retracted for 1 mm when the needle tip reached the bone, and the drug was then injected.

Measurement: thermal radiation/foot-lifting method; the rats were allowed to freely stand on a glass panel, and measurements were taken after the animals calmed down. A beam with a diameter of about 4 millimeters was emitted from the radiation source after focalized through a lens, and the radiation intensity was adjusted (about 52° C.). The radiation light source was positioned below the glass panel, and the sole of the rats' rear feet was irradiated through the glass panel. The light source was connected to a timer, i.e., a stopwatch that was activated immediately when the radiation started, and the light source automatically turned off and the timing was stopped once the rear feet of the animal was lifted. The measured time interval was the latency of the evasion reaction (foot-lifting) of the rats. The maximum of irradiation time was set as 15 sec, and recorded as 15 sec when exceeded. The duration from placement on the hotplate to retraction of the tested rear feet of rats was recorded, with each rear foot tested twice (in order to avoid burning of the sole of feet of the rats, if the duration was measured as 13 sec at the first time, a second measurement was unnecessary). The time interval between repeated measurements of the same rear foot should be more than 10 min, and the average of two measurements was the pain threshold of each rear foot.

Time of measurement: for each experimental group, foot-lifting duration at the administrated side of rats in each group before administration as well as 1 h, 2 h, 4 h, 8 h, 24 h, 32 h, 48 h, 56 h, 72 h after administration was recorded, and measured twice, the average of which two measurements was the post-drug latency (DL) of the rear foot at that side at the given point of time.

2. Measurement for motor nerve blocking: at the same time when sensory blocking was observed, a four-level rating method was used for the assessment of motor nerve blocking in rats in each treatment groups:

Level 1: claw motion was normal, capable of dorsiflexing, stretching, and eversing;

Level 2: claw was capable of dorsiflexing, stretching out again after curling (bending and adducting) with weaker stretching ability;

Level 3: claw was capable of dorsiflexing, but not able to stretching out again after curling (bending and adducting);

Level 4: claw failed to dorsiflex, stretch, or everse, and defects in gait were exhibited in rats.

Particularly, level 1 indicated no motion blocking, level 2 indicated partial motion blocking, and level 3 and 4 indicated complete motion blocking. 1 h, 2 h, 4 h, 8 h, 24 h, 32 h, 48 h, 56 h, and 72 h after administration, motion blocking at rear feet at the administrated side of rats in each group was observed, the assessed level was recorded, and the duration of motion blocking was investigated.

Statistical Processing

Statistical processing was carried out by using the SPSS software. Quantitative data was compared by one-factor variance analysis, with the results represented in average±standard deviation ($\bar{x}\pm s$). Rating levels for motion blocking were converted (level 1 was equivalent to 1, level 2 was equivalent to 2, level 3 was equivalent to 3, and level 4 was equivalent to 4), and then compared in rank sum test. $P<0.05$ indicates a statistical difference, and $P<0.01$ indicates a substantial statistical significance.

Experimental Results

Results were shown in Table VII and VIII and FIGS. 1-8. Ropivacaine sustained-release formulations of various prescribed compositions all showed some continuous analgesic effect, with part of the formulations lasting for 24 h or even more than 32 h, and different solvents in the prescribed compositions had no substantial interference with the efficacy of the principle agent, as shown in Table IX and X and FIGS. 1-8.

Experimental Example 9

Study on Efficacy of Ropivacaine Sustained-Release Formulations of Prescribed Compositions (Post-Operative Stimulation)

Experiment animals: about 70 male SD rats of 300-330 g were adaptively fed for 2-3 days, and then subjected to establishment of post-operative (hereinafter simply referred to as "P.O.") pain models.

P.O. pain model establishment: rats were anesthetized by intraperitoneal injection of 10% chloral hydrate. An incision of 1 cm in length was cut laterally across the sole of the right rear foot of the rats, with a distance of about 0.5 cm from the right heel, by using a scalpel. Thereafter, the hamstring and muscle under the skin were located and lifted up by using bend tweezers, across which was cut laterally for 3-4 times (the hamstring was maintained undetached from the muscle) to cause lesion. Blood bled out was drained with adsorbent cotton, and the skin at the sole of feet was stitched up with mattress sutures. Finally, 50 mg sodium ampicillin was intramuscularly injected in the left hind limb to prevent infection.

Experiment grouping and dosing regimen: after the operation was completed, the rats were left to recover overnight. In the morning of the next day, after the pain threshold was measured (mechanical puncture/foot-lifting method), the rats were randomly divided into 10 groups with 6 rats in each group according to their pain threshold values, which were respectively: model control group, ropivacaine methanesulfonate injection solution 1 group, ropivacaine formulation-2 group, solvent 2 group, ropivacaine formulation-3 group, solvent 3 group, ropivacaine formulation-4 group, solvent 4 group, ropivacaine formulation-5 group, and solvent 5 group (see Table VI for detailed prescribed composition and specification). The ropivacaine injection solution group, ropivacaine formulation 2-5 groups and solvent 2-5 groups were each given a dosage of 0.5 ml/rat.

Route of administration: a needle was inserted at approximately ⅓ of the connection between the right humeral motor and the ischial tuberosity of the rats, in the anteromedial direction with the end of the needle tilted up at 45°, retracted for 1 mm when the needle tip reached the bone, and the drug was finally injected.

Measurement: mechanic puncture/foot-lifting method; the rats were allowed to freely stand on a wire gauze, and measurements were taken at the right rear feet thereof by using a electronic Von Frey needle after the rats calmed down. The max value was taken as the pain threshold. Each rat was subjected to two measurements with an interval of 5 minutes or more therebetween, and the two measurements were then averaged.

Time of measurement: before administration (hereinafter abbreviated as "pre-admin."); 1 h, 2 h, 4 h, 8 h, 24 h, 32 h, 48 h, 56 h, 72 h after administration.

Data analysis: statistical processing was carried out by using the SPSS software. Quantitative data was compared by one-factor variance analysis, represented in average±standard deviation ($\bar{x}$±s). P<0.05 indicates a statistical difference, and P<0.01 indicates a substantial statistical significance.

TABLE VI

Prescribed Composition for P.O. pain experiments

| No. | Prescribed composition | Incorporated drug | Concentration (mg/ml) | Measured concentration (mg/ml) |
|---|---|---|---|---|
| 1 | Water for injection (100%)/medicinal grade sodium chloride | ropivacaine methanesulfonate | 12 | 11.8 |
| 2 | benzyl alcohol (10%)/benzyl benzoate (15%)/castor oil (75%) | ropivacaine free base | 45 | 45.7 |
| 3 | Ethanol (10%)/benzyl benzoate (15%)/castor oil (75%) | ropivacaine free base | 50 | 49.2 |
| 4 | benzyl alcohol (10%)/benzyl benzoate (15%)/soybean oil (75%) | ropivacaine free base | 35 | 35.1 |
| 5 | anhydrous ethanol (10%)/benzyl benzoate (15%)/soybean oil (75%) | ropivacaine free base | 30 | 31.1 |

Note:
ropivacaine methanesulfonate was prepared according to commercial standards.

Figure 9:
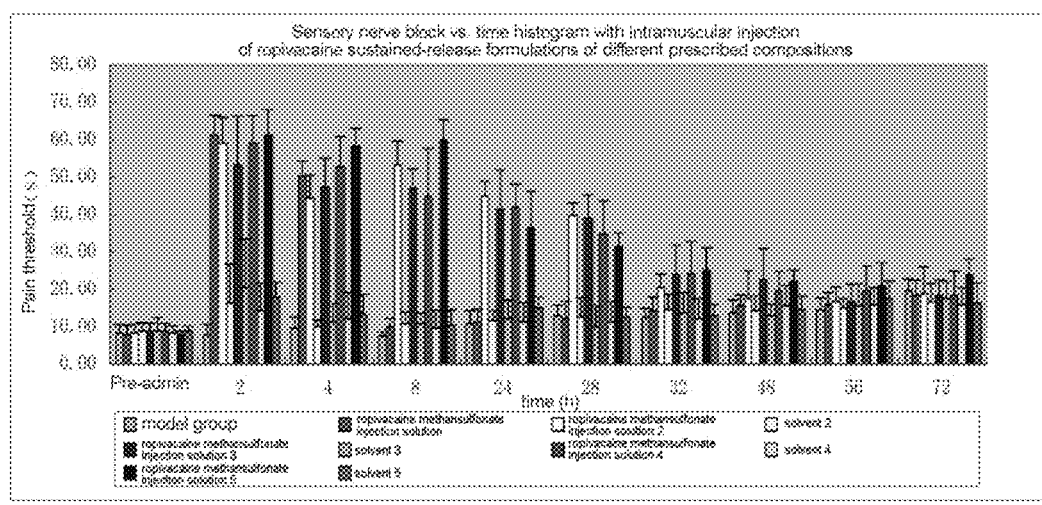
FIG. 9: Sensory nerve block vs. time histogram with intramuscular injection of ropivacaine sustained-release formulations of different prescribed compositions In these figures, the prescribed compositions 1-8 are prepared according to the formulae in Table 4.

Experimental results: as shown in Table XI and FIG. 9, the administered dosage of ropivacaine injection solution was relatively low (movement abnormality or even motality of animals might occur if the administered dosage was the same as the sustained-release formulations) and continuous analgesia might last for about 2 h; whereas, ropivacaine sustained-release formulations of various experimental compositions had a continuous analgesic duration of at least 24 h, with some prescription achieving a duration of 32 h or more, and therefore the ropivacaine sustained-release formulations exhibited a superior continuous analgesic efficacy.

TABLE VII

Statistics of sensory nerve blocking time with intramuscular injection of ropivacaine sustained-release formulations of various prescribed compositions in rats ($\bar{x}$ ± s , n = 6)

| Groups | Pre-admin. | 1 h | 2 h | 4 h | 8 h |
|---|---|---|---|---|---|
| Ropivacaine injection solution group | 8.98 ± 1.09 | 14.92 ± 0.13** | 14.77 ± 0.44** | 8.93 ± 1.67 | 8.13 ± 1.11 |
| Ropivacaine sustained-release formulation 1 group | 9.36 ± 1.31 | 14.87 ± 0.22** | 14.48 ± 0.57** | 14.27 ± 0.85** | 14.58 ± 0.54** |
| Ropivacaine sustained-release formulation 2 group | 9.30 ± 1.03 | 14.83 ± 0.32** | 14.72 ± 0.43** | 13.95 ± 1.05** | 14.45 ± 1.05** |

TABLE VII-continued

Statistics of sensory nerve blocking time with intramuscular injection of ropivacaine sustained-release formulations of various prescribed compositions in rats ($\bar{x} \pm s$, n = 6)

| | | | | | |
|---|---|---|---|---|---|
| Ropivacaine sustained-release formulation 3 group | 9.28 ± 1.66 | 14.7 ± 0.43** | 14.83 ± 0.29** | 14.18 ± 0.80** | 14.12 ± 0.99** |
| Ropivacaine sustained-release formulation 4 group | 9.03 ± 1.57 | 14.98 ± 0.04** | 14.68 ± 0.38** | 14.1 ± 1.00** | 11.18 ± 1.00** |
| Ropivacaine sustained-release formulation 5 group | 8.97 ± 1.23 | 14.95 ± 0.08** | 14.72 ± 0.43** | 14.52 ± 0.86** | 14.43 ± 0.65** |
| Ropivacaine sustained-release formulation 6 group | 9.33 ± 1.54 | 14.6 ± 1.36** | 14.68 ± 0.55** | 14.62 ± 0.51** | 14.47 ± 0.52** |
| Ropivacaine sustained-release formulation 7 group | 9.03 ± 1.52 | 14.1 ± 1.36** | 13.13 ± 1.13** | 12.5 ± 1.08** | 10.72 ± 1.76* |
| Ropivacaine sustained-release formulation 8 group | 9.07 ± 1.60 | 14.87 ± 0.21** | 14.75 ± 0.39** | 14.23 ± 0.63** | 14.37 ± 0.73** |

| Groups | 24 h | 32 h | 48 h | 56 h | 72 h |
|---|---|---|---|---|---|
| Ropivacaine injection solution group | 9.03 ± 1.31 | 9.42 ± 2.33 | 9.02 ± 1.91 | 8.82 ± 1.61 | 9.27 ± 0.97 |
| Ropivacaine sustained-release formulation 1 group | 13.63 ± 1.15** | 12.17 ± 1.70** | 10.43 ± 0.79* | 9.53 ± 1.57 | 8.93 ± 1.49 |
| Ropivacaine sustained-release formulation 2 group | 14.2 ± 1.01** | 12.38 ± 1.48** | 10.43 ± 1.40* | 9.25 ± 1.60 | 10.73 ± 2.00 |
| Ropivacaine sustained-release formulation 3 group | 11.07 ± 1.28* | 8.83 ± 1.11 | 9.1 ± 2.13 | 8.97 ± 2.28 | 9.25 ± 2.07 |
| Ropivacaine sustained-release formulation 4 group | 9.62 ± 0.60 | 8.45 ± 1.69 | 8.93 ± 1.91 | 8.42 ± 2.74 | 8.45 ± 1.58 |
| Ropivacaine sustained-release formulation 5 group | 12.42 ± 1.09** | 10.68 ± 1.65* | 9.03 ± 1.66 | 9.23 ± 1.33 | 8.52 ± 1.48 |
| Ropivacaine sustained-release formulation 6 group | 12.67 ± 0.97** | 10.83 ± 1.85* | 9.55 ± 1.30 | 9.93 ± 1.27 | 9.33 ± 1.42 |
| Ropivacaine sustained-release formulation 7 group | 11.15 ± 0.87* | 8.97 ± 1.11 | 8.62 ± 1.48 | 8.47 ± 1.65 | 8.52 ± 1.56 |

TABLE VII-continued

Statistics of sensory nerve blocking time with intramuscular injection of ropivacaine sustained-release formulations of various prescribed compositions in rats ($\bar{x} \pm s$, n = 6)

| Ropivacaine sustained-release formulation 8 group | 13.57 ± 1.27** | 10.9 ± 1.34* | 9.2 ± 1.50 | 9.52 ± 2.24 | 9.73 ± 1.79 |

Note:
as compared to the control group, **P < 0.01, *P < 0.05.

TABLE VIII

Statistics of motor nerve blocking time with intramuscular injection of ropivacaine sustained-release formulations of various prescribed compositions in rats ($\bar{x} \pm s$, n = 6)

| | Pre-admin. | 1 h | 2 h | 4 h | 8 h |
|---|---|---|---|---|---|
| Ropivacaine injection solution group | 1 ± 0.0 | 2.5 ± 0.55** | 1.83 ± 0.41** | 1.17 ± 0.41 | 1 ± 0 |
| Ropivacaine sustained-release formulation 1 group | 1 ± 0.0 | 2.33 ± 0.52** | 2 ± 0.63** | 2 ± 0.63** | 1.33 ± 0.82** |
| Ropivacaine sustained-release formulation 2 group | 1 ± 0.0 | 2 ± 0.63** | 2 ± 0.63** | 1.67 ± 0.52** | 1.5 ± 0.55** |
| Ropivacaine sustained-release formulation 3 group | 1 ± 0.0 | 2.83 ± 0.41** | 2.83 ± 0.41** | 2.33 ± 0.52** | 2.17 ± 0.41** |
| Ropivacaine sustained-release formulation 4 group | 1 ± 0.0 | 2.33 ± 0.52** | 2 ± 0.00** | 2 ± 0.00** | 1.33 ± 0.52* |
| Ropivacaine sustained-release formulation 5 group | 1 ± 0.0 | 2.5 ± 0.55** | 2.17 ± 0.41** | 2.17 ± 0.41** | 1.5 ± 0.55* |
| Ropivacaine sustained-release formulation 6 group | 1 ± 0.0 | 2.5 ± 0.55** | 2.33 ± 0.52** | 2.17 ± 0.41** | 2.17 ± 0.41** |
| Ropivacaine sustained-release formulation 7 group | 1 ± 0.0 | 2.5 ± 0.55** | 2.17 ± 0.41** | 2.17 ± 0.41** | 1.5 ± 0.84** |
| Ropivacaine sustained-release formulation 8 group | 1 ± 0.0 | 2 ± 0.63** | 2.33 ± 0.52** | 1.83 ± 0.75** | 1.83 ± 0.75** |

| | 24 h | 32 h | 48 h | 56 h | 72 h |
|---|---|---|---|---|---|
| Ropivacaine injection solution group | 1 ± 0 | 1 ± 0 | 1 ± 0 | 1 ± 0 | 1 ± 0 |
| Ropivacaine sustained-release formulation 1 group | 1.17 ± 0.41* | 1 ± 0 | 1 ± 0 | 1 ± 0 | 1 ± 0 |

TABLE VIII-continued

Statistics of motor nerve blocking time with intramuscular injection of ropivacaine sustained-release formulations of various prescribed compositions in rats ($\bar{x} \pm s$, n = 6)

| | | | | | |
|---|---|---|---|---|---|
| Ropivacaine sustained-release formulation 2 group | 1.33 ± 0.52* | 1 ± 0 | 1 ± 0 | 1 ± 0 | 1 ± 0 |
| Ropivacaine sustained-release formulation 3 group | 2.17 ± 0.41** | 1.33 ± 0.52* | 1.17 ± 0.41 | 1.17 ± 0.41 | 1.17 ± 0.41 |
| Ropivacaine sustained-release formulation 4 group | 1.33 ± 0.52* | 1 ± 0 | 1 ± 0 | 1 ± 0 | 1 ± 0 |
| Ropivacaine sustained-release formulation 5 group | 1.17 ± 0.41 | 1.17 ± 0.41 | 1.17 ± 0.41 | 1 ± 0 | 1 ± 0 |
| Ropivacaine sustained-release formulation 6 group | 2 ± 0** | 1.33 ± 0.52* | 1 ± 0 | 1 ± 0 | 1 ± 0 |
| Ropivacaine sustained-release formulation 7 group | 1.5 ± 0.84** | 1.17 ± 0.41 | 1.17 ± 0.41 | 1.17 ± 0.41 | 1 ± 0 |
| Ropivacaine sustained-release formulation 8 group | 1.83 ± 0.75** | 1.17 ± 0.41 | 1.17 ± 0.41 | 1.17 ± 0.41 | 1 ± 0 |

Note:
as compared to the control group, **$P < 0.01$, *$P < 0.05$.

TABLE IX

Statistics of sensory nerve blocking time with intramuscular injection of solvents in ropivacaine sustained-release formulations of various prescribed compositions in rats ($\bar{x} \pm s$, n = 6)

| | Pre-admin. | 1 h | 2 h | 4 h | 8 h |
|---|---|---|---|---|---|
| Ropivacaine injection solution group | 8.98 ± 1.09 | 14.92 ± 0.13** | 14.77 ± 0.44** | 8.93 ± 1.67 | 8.13 ± 1.11 |
| Solvent 1 group | 9.15 ± 1.03 | 12.9 ± 1.28** | 12.85 ± 0.85** | 12.4 ± 1.33** | 10.8 ± 0.32** |
| Solvent 2 group | 9.28 ± 0.97 | 12.62 ± 1.05** | 12.1 ± 1.39** | 11.68 ± 0.91* | 11.25 ± 0.92** |
| Solvent 3 group | 8.97 ± 1.91 | 8.9 ± 1.37 | 8.82 ± 1.55 | 8.25 ± 1.34 | 8.87 ± 1.71 |
| Solvent 4 group | 8.88 ± 1.51 | 8.93 ± 1.62 | 8.08 ± 1.24 | 9.5 ± 1.24 | 9.15 ± 1.68 |
| Solvent 5 group | 9.3 ± 1.78 | 13.15 ± 1.66** | 10.33 ± 1.78 | 9.43 ± 1.30 | 8.6 ± 2.48 |
| Solvent 6 group | 8.87 ± 1.68 | 9.7 ± 1.46 | 8.42 ± 1.38 | 8.55 ± 1.05 | 8.68 ± 1.72 |
| Solvent 7 group | 8.92 ± 1.43 | 12.43 ± 1.67** | 11.07 ± 0.72* | 8.35 ± 2.11 | 8.57 ± 1.25 |
| Solvent 8 group | 8.72 ± 1.17 | 8.9 ± 1.29 | 9.12 ± 1.16 | 8.95 ± 1.87 | 9.05 ± 1.57 |
| | 24 h | 32 h | 48 h | 56 h | 72 h |
| Ropivacaine injection solution group | 9.03 ± 1.31 | 9.42 ± 2.33 | 9.02 ± 1.91 | 8.82 ± 1.61 | 9.27 ± 0.97 |

TABLE IX-continued

Statistics of sensory nerve blocking time with intramuscular injection of solvents in ropivacaine sustained-release formulations of various prescribed compositions in rats ($\bar{x} \pm s$, n = 6)

| Solvent 1 group | 10.17 ± 1.40 | 9.28 ± 12.23 | 8.68 ± 2.18 | 9.05 ± 1.26 | 8.7 ± 1.61 |
|---|---|---|---|---|---|
| Solvent 2 group | 10.28 ± 1.02 | 10.02 ± 2.01 | 9.02 ± 1.72 | 9.68 ± 1.60 | 9.5 ± 1.99 |
| Solvent 3 group | 9.5 ± 1.11 | 9 ± 1.32 | 8.92 ± 1.53 | 9.23 ± 1.79 | 9.02 ± 1.60 |
| Solvent 4 group | 8.47 ± 1.62 | 8.93 ± 2.28 | 8.7 ± 1.76 | 9.22 ± 2.36 | 9.22 ± 1.80 |
| Solvent 5 group | 8.55 ± 1.54 | 8.73 ± 2.05 | 9.13 ± 1.08 | 8.83 ± 1.37 | 9.1 ± 1.46 |
| Solvent 6 group | 8.78 ± 1.49 | 9.07 ± 1.85 | 9.2 ± 1.41 | 8.68 ± 1.41 | 9.03 ± 1.58 |
| Solvent 7 group | 8.95 ± 1.30 | 8.53 ± 1.19 | 8.83 ± 1.63 | 8.98 ± 1.20 | 8.38 ± 1.25 |
| Solvent 8 group | 8.47 ± 1.34 | 8.95 ± 1.65 | 8.72 ± 1.53 | 8.67 ± 0.83 | 9 ± 1.34 |

Note:
as compared to the control group, **P < 0.01, *P < 0.05.

TABLE X

Statistics of motor nerve blocking time with intramuscular injection of solvents in ropivacaine sustained-release formulations of various prescribed compositions in rats ($\bar{x} \pm s$, n = 6)

| | Pre-admin. | 1 h | 2 h | 4 h | 8 h | 24 h | 32 h | 48 h | 56 h | 72 h |
|---|---|---|---|---|---|---|---|---|---|---|
| ropivacaine injection solution group | 1 ± 0 | 2.5 ± 0.55** | 1.83 ± 0.41** | 1.17 ± 0.41 | 1 ± 0 | 1 ± 0 | 1 ± 0 | 1 ± 0 | 1 ± 0 | 1 ± 0 |
| Solvent 1 group | 1 ± 0 | 2 ± 0.89** | 1.67 ± 0.52** | 1.67 ± 0.52** | 1 ± 0 | 1 ± 0 | 1 ± 0 | 1 ± 0 | 1 ± 0 | 1 ± 0 |
| Solvent 2 group | 1 ± 0 | 2.17 ± 0.75** | 1.17 ± 0.41 | 1.17 ± 0.41 | 1 ± 0 | 1 ± 0 | 1 ± 0 | 1 ± 0 | 1 ± 0 | 1 ± 0 |
| Solvent 3 group | 1 ± 0 | 2.33 ± 0.52** | 1.5 ± 0.55* | 1 ± 0 | 2.33 ± 0.52** | 1 ± 0 | 1 ± 0 | 1 ± 0 | 1 ± 0 | 1 ± 0 |
| Solvent 4 group | 1 ± 0 | 2.17 ± 0.41** | 1.67 ± 0.52* | 1 ± 0 | 1 ± 0 | 1 ± 0 | 1 ± 0 | 1 ± 0 | 1 ± 0 | 1 ± 0 |
| Solvent 5 group | 1 ± 0 | 2.17 ± 0.41** | 1.33 ± 0.52* | 1 ± 0 | 1 ± 0 | 1 ± 0 | 1 ± 0 | 1 ± 0 | 1 ± 0 | 1 ± 0 |
| Solvent 6 group | 1 ± 0 | 1.67 ± 0.52* | 1.33 ± 0.52* | 1 ± 0 | 1 ± 0 | 1 ± 0 | 1 ± 0 | 1 ± 0 | 1 ± 0 | 1 ± 0 |
| Solvent 7 group | 1 ± 0 | 2.33 ± 0.52** | 1.83 ± 0.41** | 1.67 ± 0.82** | 1 ± 0 | 1 ± 0 | 1 ± 0 | 1 ± 0 | 1 ± 0 | 1 ± 0 |
| Solvent 8 group | 1 ± 0 | 1.83 ± 0.75** | 1.17 ± 0.41 | 1.17 ± 0.41 | 1 ± 0 | 1 ± 0 | 1 ± 0 | 1 ± 0 | 1 ± 0 | 1 ± 0 |

Note:
as compared to the control group, **P < 0.01, *P < 0.05.

TABLE XI

Statistics of sensory nerve blocking time with intramuscular injection of ropivacaine sustained-release formulations of various prescribed compositions in rats (P.O. pain model) ($\bar{x} \pm s$, n = 6)

| Time | 1 h | 2 h | 4 h | 8 h | 24 h |
|---|---|---|---|---|---|
| Model group | 8.18 ± 2.44 | 7.8 ± 2.79 | 9.73 ± 2.92 | 7.43 ± 1.15 | 10.83 ± 3.41 |
| Ropivacaine methanesulfonate injection solution 1 group | 8.02 ± 2.45 | 61.25 ± 5.28** | 50.47 ± 3.90** | 10.2 ± 1.99** | 11.4 ± 3.32 |
| Ropivacaine sustained-release formulation 2 group | 8.35 ± 2.36 | 59.3 ± 6.75** | 44.51 ± 6.05** | 53.32 ± 6.42** | 45.05 ± 3.93** |
| Solvent 2 group | 8.83 ± 2.34 | 16.2 ± 10.50** | 9.8 ± 1.92 | 10.63 ± 3.25* | 11.77 ± 2.54 |
| Ropivacaine sustained-release formulation 3 group | 8.55 ± 2.37 | 53.17 ± 13.13** | 47.58 ± 7.44** | 47.17 ± 5.16** | 41.67 ± 10.18** |
| Solvent 3 group | 8.87 ± 3.63 | 20.65 ± 12.83** | 11.45 ± 4.68 | 10.75 ± 2.83* | 11.95 ± 5.21 |
| Ropivacaine sustained-release formulation 4 group | 8.58 ± 2.28 | 59.3 ± 7.21** | 52.8 ± 7.99** | 44.93 ± 12.88** | 41.92 ± 6.33** |

TABLE XI-continued

Statistics of sensory nerve blocking time with intramuscular injection of ropivacaine sustained-release formulations of various prescribed compositions in rats (P.O. pain model) ($\bar{x} \pm s$, n = 6)

| | | | | | |
|---|---|---|---|---|---|
| Solvent 4 group | 8.37 ± 1.85 | 14.33 ± 7.34* | 12.05 ± 7.15 | 9.57 ± 4.91 | 11.25 ± 5.22 |
| Ropivacaine sustained-release formulation 5 group | 7.80 ± 1.07 | 61.43 ± 6.72** | 58.45 ± 4.67** | 59.88 ± 5.49** | 36.40 ± 9.81** |
| Solvent 5 group | 8.60 ± 1.50 | 17.93 ± 3.93 | 13.20 ± 5.57 | 10.38 ± 4.15 | 14.87 ± 3.08 |

| Time | 28 h | 32 h | 48 h | 56 h | 72 h |
|---|---|---|---|---|---|
| Model group | 13.13 ± 2.67 | 12.32 ± 2.56 | 13.87 ± 3.32 | 14.68 ± 2.99 | 19.55 ± 3.19 |
| Ropivacaine methanesulfonate injection solution 1 group | 12.25 ± 4.58 | 14.23 ± 3.74 | 15.48 ± 3.04 | 16.03 ± 3.14 | 18.22 ± 4.20 |
| Ropivacaine sustained-release formulation 2 group | 39.72 ± 3.41** | 20.58 ± 3.50** | 17.65 ± 7.34* | 16.57 ± 4.05 | 18.92 ± 7.13 |
| Solvent 2 group | 12.57 ± 5.17 | 14.8 ± 3.86 | 14.13 ± 4.15 | 15.03 ± 2.51 | 16.57 ± 5.06 |
| Ropivacaine sustained-release formulation 3 group | 38.82 ± 6.54** | 23.88 ± 8.01** | 22.42 ± 8.56* | 16.53 ± 4.92 | 18.5 ± 4.03 |
| Solvent 3 group | 10.1 ± 5.52 | 13.82 ± 5.33 | 13.03 ± 3.05 | 15.42 ± 6.13 | 17.63 ± 4.56 |
| Ropivacaine sustained-release formulation 4 group | 34.72 ± 8.87** | 24.43 ± 8.43** | 19.52 ± 5.29* | 19.47 ± 6.82* | 18.53 ± 6.35 |
| Solvent 4 group | 11.07 ± 5.71 | 12.13 ± 5.36 | 15.4 ± 5.66 | 16.03 ± 4.47 | 15.72 ± 4.80 |
| Ropivacaine sustained-release formulation 5 group | 31.42 ± 3.74** | 25.30 ± 5.81** | 22.17 ± 2.93* | 20.77 ± 6.35 | 23.73 ± 4.41 |
| Solvent 5 group | 12.68 ± 2.53 | 12.80 ± 3.19 | 14.8 ± 3.37 | 17.42 ± 4.86 | 16.45 ± 5.25 |

Note:
as compared to the control group, **P < 0.01, *P < 0.05.

BEST MODE FOR CARRYING OUT THE INVENTION

Example 1

Formula: Ropivacaine Free Base

| 10 mg | benzyl alcohol |
|---|---|
| 0.1 ml | ethyl oleate (or vegetable oil such as soybean oil) to a total of 10 ml |

Preparation process: 10 mg ropivacaine free base was added into a prescribed amount of benzyl alcohol until it was fully dissolved to obtain a drug solution; ethyl oleate (or vegetable oil such as soybean oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 2

Formula: Ropivacaine Free Base

| 1600 mg | benzyl alcohol |
|---|---|
| 7.5 ml | ethyl oleate (or vegetable oil such as soybean oil) to a total of 2.5 ml |

Preparation process: 1600 mg ropivacaine free base was slowly added in batches into a prescribed amount of benzyl alcohol, and vortexed until it was fully dissolved to obtain a drug solution; ethyl oleate (or vegetable oil such as soybean oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 3

Formula: Ropivacaine Free Base

| 10 mg | ethanol |
|---|---|
| 0.1 ml | ethyl oleate (or castor oil) to a total of 10 ml |

Preparation process: 10 mg ropivacaine free base was slowly added into a prescribed amount of ethanol, and vortexed until it was fully dissolved to obtain a drug solution; ethyl oleate (or castor oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 4

Formula: Ropivacaine Free Base

| | |
|---|---|
| 750 mg | ethanol |
| 5 ml | ethyl oleate (or castor oil) to a total of 10 ml |

Preparation process: 750 mg ropivacaine free base was slowly added in batches into a prescribed amount of ethanol, and vortexed until it was fully dissolved to obtain a drug solution; ethyl oleate (or castor oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 5

Formula: Ropivacaine Free Base

| | |
|---|---|
| 10 mg | benzyl benzoate |
| 0.1 ml | ethyl oleate (or vegetable oil such as soybean oil) to a total of 10 ml |

Preparation process: 10 mg ropivacaine free base was added into a prescribed amount of benzyl benzoate, and vortexed until it was fully dissolved to obtain a drug solution; ethyl oleate (or vegetable oil such as soybean oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 6

Formula: Ropivacaine Free Base

| | |
|---|---|
| 500 mg | benzyl benzoate |
| 7 ml | ethyl oleate (or vegetable oil such as soybean oil) to a total of 10 ml |

Preparation process: 500 mg ropivacaine free base was slowly added into a prescribed amount of benzyl benzoate, and vortexed until it was fully dissolved to obtain a drug solution; ethyl oleate (or vegetable oil such as soybean oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 7

Formula: Ropivacaine Free Base

| | |
|---|---|
| 50 mg | benzyl alcohol |
| 0.1 ml | ethyl oleate (or vegetable oil such as soybean oil) to a total of 10 ml |

Preparation process: 50 mg ropivacaine free base was added into a prescribed amount of benzyl alcohol and a small amount of ethyl oleate (or vegetable oil such as soybean oil), and vortexed until it was fully dissolved to obtain a drug solution; ethyl oleate (or vegetable oil such as soybean oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 8

Formula: Ropivacaine Free Base

| | |
|---|---|
| 1000 mg | benzyl alcohol |
| 4 ml | ethyl oleate (or vegetable oil such as soybean oil) to a total of 10 ml |

Preparation process: 1000 mg ropivacaine free base was slowly added into a prescribed amount of benzyl alcohol, and vortexed until it was fully dissolved to obtain a drug solution; ethyl oleate (or vegetable oil such as soybean oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 9

Formula: Ropivacaine Free Base

| | |
|---|---|
| 50 mg | ethanol |
| 0.1 ml | ethyl oleate (or castor oil) to a total of 10 ml |

Preparation process: 50 mg ropivacaine free base was added into a prescribed amount of ethanol and a small amount of ethyl oleate (or castor oil), and vortexed until it was fully dissolved to obtain a drug solution; ethyl oleate (or castor oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 10

Formula: Ropivacaine Free Base

| | |
|---|---|
| 600 mg | ethanol |
| 4 ml | ethyl oleate (or castor oil) to a total of 10 ml |

Preparation process: 600 mg ropivacaine free base was added into a prescribed amount of ethanol, and vortexed until it was fully dissolved to obtain a drug solution; ethyl oleate (or castor oil) was then slowly added into the drug solution to a total of 10 ml and uniformly mixed with vortexing; the mixture was filtered through a film to remove

Example 11

Formula: Ropivacaine Free Base

| | |
|---|---|
| 300 mg | benzyl alcohol |
| 1 ml | ethyl oleate to a total of 10 ml |

Preparation process: 300 mg ropivacaine free base was slowly added into a prescribed amount of benzyl alcohol, heated gently and vortexed until it was fully dissolved to obtain a drug solution; ethyl oleate was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 12

Formula: Ropivacaine Free Base

| | |
|---|---|
| 250 mg | ethanol |
| 1 ml | ethyl oleate to a total of 10 ml |

Preparation process: 250 mg ropivacaine free base was slowly added into a prescribed amount of ethanol, heated gently and vortexed until it was fully dissolved to obtain a drug solution; ethyl oleate was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 13

Formula: Ropivacaine Free Base

| | |
|---|---|
| 450 mg | ethanol |
| 0.8 ml | benzyl alcohol |
| 0.8 ml | ethyl oleate to a total of 10 ml |

Preparation process: 450 mg ropivacaine free base was slowly added into a prescribed amount of benzyl alcohol and ethanol, heated gently and vortexed until it was fully dissolved to obtain a drug solution; ethyl oleate was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 14

Formula: Ropivacaine Free Base

| | |
|---|---|
| 350 mg | benzyl alcohol |
| 1 ml | castor oil to a total of 10 ml |

Preparation process: 350 mg ropivacaine free base was slowly added into a prescribed amount of benzyl alcohol, heated gently and vortexed until it was fully dissolved to obtain a drug solution; castor oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 15

Formula: Ropivacaine Free Base

| | |
|---|---|
| 300 mg | benzyl alcohol |
| 1 ml | soybean oil to a total of 10 ml |

Preparation process: 300 mg ropivacaine free base was slowly added into a prescribed amount of benzyl alcohol, heated gently and vortexed until it was fully dissolved to obtain a drug solution; soybean oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 16

Formula: Ropivacaine Free Base

| | |
|---|---|
| 250 mg | ethanol |
| 1 ml | castor oil to a total of 10 ml |

Preparation process: 250 mg ropivacaine free base was slowly added into a prescribed amount of ethanol, heated gently and vortexed until it was fully dissolved to obtain a drug solution; castor oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 17

Formula: Ropivacaine Free Base

| | |
|---|---|
| 300 mg | benzyl alcohol |
| 1 ml | ethyl oleate |
| 3 ml | soybean oil to a total of 10 ml |

Preparation process: 300 mg ropivacaine free base was slowly added into a prescribed amount of benzyl alcohol and ethyl oleate, heated gently and vortexed until it was fully dissolved to obtain a drug solution; soybean oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 18

Formula: Ropivacaine Free Base

| 300 mg | benzyl alcohol |
| 1 ml | benzyl benzoate |
| 3 ml | soybean oil to a total of 10 ml |

Preparation process: 300 mg ropivacaine free base was added into a prescribed amount of benzyl alcohol and benzyl benzoate, heated gently and vortexed until it was fully dissolved to obtain a drug solution; soybean oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 19

Formula: Ropivacaine Free Base

| 250 mg | ethanol |
| 1 ml | ethyl oleate |
| 3 ml | soybean oil to a total of 10 ml |

Preparation process: 250 mg ropivacaine free base was added into a prescribed amount of ethanol and ethyl oleate, and vortexed until it was fully dissolved to obtain a drug solution; soybean oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 20

Formula: Ropivacaine Free Base

| 300 mg | ethanol |
| 1 ml | benzyl benzoate |
| 3 ml | soybean oil to a total of 10 ml |

Preparation process: 300 mg ropivacaine free base was added into a prescribed amount of ethanol and benzyl benzoate, heated gently and vortexed until it was fully dissolved to obtain a drug solution; soybean oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 21

Formula: Ropivacaine Free Base

| 450 mg | benzyl alcohol |
| 1 ml | benzyl benzoate |
| 1.5 ml | castor oil to a total of 10 ml |

Preparation process: 450 mg ropivacaine free base was slowly added into a prescribed amount of benzyl alcohol and benzyl benzoate, heated gently and vortexed until it was fully dissolved to obtain a drug solution; castor oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 22

Formula: Ropivacaine Free Base

| 300 mg | ethanol |
| 1 ml | ethyl oleate |
| 3 ml | castor oil to a total of 10 ml |

Preparation process: 300 mg ropivacaine free base was slowly added into a prescribed amount of ethanol and ethyl oleate, heated gently and vortexed until it was fully dissolved to obtain a drug solution; castor oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 23

Formula: Ropivacaine Free Base

| 400 mg | ethanol |
| 1 ml | benzyl benzoate |
| 1.5 ml | castor oil to a total of 10 ml |

Preparation process: 400 mg ropivacaine free base was slowly added into a prescribed amount of ethanol and benzyl benzoate, heated gently and vortexed until it was fully dissolved to obtain a drug solution; castor oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 24

Formula: Ropivacaine Free Base

| | |
|---|---|
| 500 mg | ethanol |
| 1 ml | benzyl benzoate |
| 3 ml | castor oil to a total of 10 ml |

Preparation process: 500 mg ropivacaine free base was added into a prescribed amount of ethanol and benzyl benzoate, heated gently and vortexed until it was fully dissolved to obtain a drug solution; castor oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 25

Formula: Ropivacaine Methanesulfonate

| | |
|---|---|
| 120 mg | ethanol |
| 1.8 ml | ethyl oleate 10 ml |

Preparation process: 120 mg ropivacaine methanesulfonate was added into a prescribed amount of ethanol, and vortexed until it was fully dissolved to obtain a drug solution; ethyl oleate was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 26

Formula: Ropivacaine Methanesulfonate

| | |
|---|---|
| 120 mg | benzyl alcohol |
| 1.6 ml | ethyl oleate (or vegetable oil such as soybean oil) to a total of 10 ml |

Preparation process: 120 mg ropivacaine methanesulfonate was added into a prescribed amount of benzyl alcohol, and vortexed until it was fully dissolved to obtain a drug solution; ethyl oleate (or vegetable oil such as soybean oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 27

Formula: Ropivacaine Methanesulfonate

| | |
|---|---|
| 120 mg | benzyl alcohol |
| 0.8 ml | ethanol |
| 0.8 ml | ethyl oleate (or vegetable oil such as soybean oil) to a total of 10 ml |

Preparation process: 120 mg ropivacaine methanesulfonate was added into a prescribed amount of benzyl alcohol and ethanol, and vortexed until it was fully dissolved to obtain a drug solution; ethyl oleate (or vegetable oil such as soybean oil) was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 28

Formula: Ropivacaine Free Base

| | |
|---|---|
| 450 mg | ethyl lactate |
| 5 ml | ethyl oleate to a total of 10 ml |

Preparation process: 450 mg ropivacaine free base was slowly added into a prescribed amount of ethyl lactate, heated gently and vortexed until it was fully dissolved to obtain a drug solution; ethyl oleate was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 29

Formula: Ropivacaine Free Base

| | |
|---|---|
| 400 mg | ethyl lactate |
| 5 ml | glyceryl triacetate to a total of 10 ml |

Preparation process: 400 mg ropivacaine free base was added into a prescribed amount of ethyl lactate, and vortexed until it was fully dissolved to obtain a drug solution; glyceryl triacetate was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 30

Formula: Ropivacaine Free Base

| | |
|---|---|
| 350 mg | ethanol |
| 0.6 ml | benzyl alcohol |
| 0.8 ml | ethyl oleate |
| 4 ml | soybean oil to a total of 10 ml |

Preparation process: 350 mg ropivacaine free base was slowly added into a prescribed amount of ethanol and benzyl alcohol, heated gently and vortexed until it was fully dissolved to obtain a drug solution; 4 ml ethyl oleate was slowed added into the drug solution and uniformly mixed, and soybean oil was then slowly added to a total of 10 ml and uniformly mixed with vortexing; the mixture was filtered through a film to remove impurities and bacteria,

Example 31

Formula: Ropivacaine Free Base

| | |
|---|---|
| 250 mg | ethanol |
| 1 ml | castor oil (containing 15% (w/v) hydrogenated castor oil) to a total of 10 ml |

Preparation process: 250 mg ropivacaine free base was slowly added into a prescribed amount of ethanol, heated gently and vortexed until it was fully dissolved to obtain a drug solution; castor oil (containing 15% (w/v) hydrogenated castor oil) was then slowly added to a total of 10 ml and uniformly mixed with vortexing; the mixture was filtered through a film to remove impurities and bacteria, separately charged into penicillin bottles and sealed, and then packed after passing lamp inspection.

Example 32

Formula: Ropivacaine Free Base

| | |
|---|---|
| 300 mg | benzyl alcohol |
| 1 ml | castor oil (containing 15% (w/v) hydrogenated castor oil) to a total of 10 ml |

Preparation process: 300 mg ropivacaine free base was slowly added into a prescribed amount of benzyl alcohol, heated gently and vortexed until it was fully dissolved to obtain a drug solution; castor oil (containing 15% (w/v) hydrogenated castor oil) was then slowly added to a total of 10 ml and uniformly mixed with vortexing; the mixture was filtered through a film to remove impurities and bacteria, separately charged into penicillin bottles and sealed, and then packed after passing lamp inspection.

Example 33

Formula: Ropivacaine Free Base

| | |
|---|---|
| 300 mg | benzyl alcohol |
| 1 ml | soybean oil (containing 15% (w/v) white oil) to a total of 10 ml |

Preparation process: 300 mg ropivacaine free base was slowly added into a prescribed amount of benzyl alcohol, heated gently and vortexed until it was fully dissolved to obtain a drug solution; soybean oil (containing 15% (w/v) white oil) was then slowly added to a total of 10 ml and uniformly mixed with vortexing; the mixture was filtered through a film to remove impurities and bacteria, separately charged into penicillin bottles and sealed, and then packed after passing lamp inspection.

Example 34

Formula: Ropivacaine Free Base

| | |
|---|---|
| 350 mg | dezocine |
| 350 mg | benzyl alcohol |
| 1 ml | benzyl benzoate |
| 1.5 ml | soybean oil to a total of 10 ml |

Preparation process: 350 mg ropivacaine free base and 350 mg dezocine was slowly added into a prescribed amount of benzyl alcohol and benzyl benzoate, heated gently and vortexed until it was fully dissolved to obtain a drug solution; soybean oil was then slowly added to a total of 10 ml and uniformly mixed with vortexing; the mixture was filtered through a film to remove impurities and bacteria, separately charged into penicillin bottles and sealed, and then packed after passing lamp inspection.

Example 35

Formula: Ropivacaine Free Base

| | |
|---|---|
| 300 mg | dezocine |
| 350 mg | anhydrous ethanol |
| 1 ml | benzyl benzoate |
| 1.5 ml | soybean oil to a total of 10 ml |

Preparation process: 300 mg ropivacaine free base and 350 mg dezocine was slowly added into a prescribed amount of anhydrous ethanol and benzyl benzoate, heated gently and vortexed until it was fully dissolved to obtain a drug solution; soybean oil was then slowly added to a total of 10 ml and uniformly mixed with vortexing; the mixture was filtered through a film to remove impurities and bacteria, separately charged into penicillin bottles and sealed, and then packed after passing lamp inspection.

Example 36

Formula: Ropivacaine Free Base

| | |
|---|---|
| 450 mg | dezocine |
| 400 mg | benzyl alcohol |
| 1 ml | benzyl benzoate |
| 1.5 ml | castor oil to a total of 10 ml |

Preparation process: 450 mg ropivacaine free base and 400 mg dezocine was slowly added into a prescribed amount of benzyl alcohol and benzyl benzoate, heated gently and vortexed until it was fully dissolved to obtain a drug solution; castor oil was then slowly added to a total of 10 ml and uniformly mixed with vortexing; the mixture was filtered through a film to remove impurities and bacteria, separately charged into penicillin bottles and sealed, and then packed after passing lamp inspection.

Example 37

Formula: Ropivacaine Free Base

| | |
|---|---|
| 300 mg | dezocine |
| 350 mg | benzyl alcohol |
| 1 ml | ethyl oleate |
| 3 ml | soybean oil to a total of 10 ml |

Preparation process: 300 mg ropivacaine free base and 350 mg dezocine was slowly added into a prescribed amount of benzyl alcohol, heated gently and vortexed until it was fully dissolved to obtain a drug solution; a prescribed amount of ethyl oleate was added thereinto and uniformly mixed, and soybean oil was then slowly added to a total of 10 ml and uniformly mixed with vortexing; the mixture was filtered through a film to remove impurities and bacteria, separately charged into penicillin bottles and sealed, and then packed after passing lamp inspection.

Example 38

Formula: Ropivacaine Free Base

| | |
|---|---|
| 350 mg | parecoxib |
| 350 mg | benzyl alcohol |
| 1 ml | benzyl benzoate |
| 1.5 ml | soybean oil to a total of 10 ml |

Preparation process: 350 mg ropivacaine free base and 350 mg parecoxib was slowly added into a prescribed amount of benzyl alcohol and benzyl benzoate, heated gently and vortexed until it was fully dissolved to obtain a drug solution; soybean oil was then slowly added to a total of 10 ml and uniformly mixed with vortexing; the mixture was filtered through a film to remove impurities and bacteria, separately charged into penicillin bottles and sealed, and then packed after passing lamp inspection.

Example 39

Formula: Ropivacaine Free Base

| | |
|---|---|
| 300 mg | parecoxib |
| 250 mg | benzyl alcohol |
| 1 ml | soybean oil to a total of 10 ml |

Preparation process: 300 mg ropivacaine free base and 250 mg parecoxib was slowly added into a prescribed amount of benzyl alcohol, heated gently and vortexed until it was fully dissolved to obtain a drug solution; soybean oil was then slowly added to a total of 10 ml and uniformly mixed with vortexing; the mixture was filtered through a film to remove impurities and bacteria, separately charged into penicillin bottles and sealed, and then packed after passing lamp inspection.

Example 40

Formula: Ropivacaine Free Base

| | |
|---|---|
| 450 mg | parecoxib |
| 450 mg | benzyl alcohol |
| 0.8 ml | anhydrous ethanol |
| 0.8 ml | ethyl oleate to a total of 10 ml |

Preparation process: 450 mg ropivacaine free base and 450 mg parecoxib was slowly added into a prescribed amount of benzyl alcohol and anhydrous ethanol, heated gently and vortexed until it was fully dissolved to obtain a drug solution; ethyl oleate was then slowly added to a total of 10 ml and uniformly mixed with vortexing; the mixture was filtered through a film to remove impurities and bacteria, separately charged into penicillin bottles and sealed, and then packed after passing lamp inspection.

Example 41

Formula: Ropivacaine Free Base

| | |
|---|---|
| 400 mg | parecoxib |
| 350 mg | benzyl alcohol |
| 1.0 ml | castor oil to a total of 10 ml |

Preparation process: 400 mg ropivacaine free base and 350 mg parecoxib was slowly added into a prescribed amount of benzyl alcohol, heated gently and vortexed until it was fully dissolved to obtain a drug solution; castor oil was then slowly added to a total of 10 ml and uniformly mixed with vortexing; the mixture was filtered through a film to remove impurities and bacteria, separately charged into penicillin bottles and sealed, and then packed after passing lamp inspection.

Example 42

Formula: Procaine Free Base

| | |
|---|---|
| 150 mg | benzyl alcohol |
| 1.0 ml | benzyl benzoate |
| 3.0 ml | castor oil to a total of 10 ml |

Preparation process: 150 mg procaine free base was slowly added into a prescribed amount of benzyl alcohol and benzyl benzoate, and vortexed until it was fully dissolved to obtain a drug solution; castor oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 43

Formula: Dibucaine Free Base

| | |
|---|---|
| 150 mg | benzyl alcohol |
| 1.0 ml | benzyl benzoate |
| 3.0 ml | castor oil to a total of 10 ml |

Preparation process: 150 mg dibucaine free base was slowly added into a prescribed amount of benzyl alcohol and benzyl benzoate, heated gently and vortexed until it was fully dissolved to obtain a drug solution; castor oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

Example 44

Formula: Articaine Free Base

| | |
|---|---|
| 180 mg | ethanol |
| 1.0 ml | benzyl benzoate |
| 3.0 ml | soybean oil to a total of 10 ml |

Preparation process: 180 mg etidocaine free base was slowly added into a prescribed amount of ethanol and benzyl benzoate, heated gently and vortexed until it was fully dissolved to obtain a drug solution; soybean oil was then slowly added into the drug solution to a total of 10 ml and uniformly mixed with vortexing; the mixture was filtered through a film to remove impurities and bacteria, separately charged into penicillin bottles and sealed, and then packed after passing lamp inspection.

What is claimed is:

1. A non-addictive sustained-release drug delivery system comprising:
   i) 12-50 mg/ml (w/v) of an anesthetic analgesic comprising a local anesthetic or a combination of a local anesthetic and at least one of parecoxib or dezocine;
   ii) 10%-40% (v/v) of a drug menstruum comprising benzyl alcohol and/or benzyl benzoate, or a combination of ethanol together with benzyl alcohol and/or benzyl benzoate; and
   iii) 60%-90% (v/v) of a drug sustained-release agent comprising soybean oil and/or castor oil,
   wherein the local anesthetic is selected from the group consisting of ropivacaine free base or a methanesulfonate, hydrochloride, citrate, sulfate, lactate, succinate, fumarate, glutamate, ethylsulfonate, benzenesulfonate, salicylate, or maleate salt thereof, and
   wherein the non-addictive sustained-release drug delivery system is oily, homogenous, and configured for injection.

2. The non-addictive sustained-release drug delivery system of claim 1, wherein the anesthetic analgesic is ropivacaine free base.

* * * * *